(12) United States Patent
Pollner et al.

(10) Patent No.: US 11,118,237 B2
(45) Date of Patent: Sep. 14, 2021

(54) COMPOSITIONS AND METHODS FOR AMPLIFYING AND CHARACTERIZING HCV NUCLEIC ACID

(71) Applicant: GEN-PROBE INCORPORATED, San Diego, CA (US)

(72) Inventors: Reinhold B. Pollner, San Diego, CA (US); Shyun-Shyun Lee, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 178 days.

(21) Appl. No.: 16/212,539

(22) Filed: Dec. 6, 2018

(65) Prior Publication Data

US 2019/0093183 A1 Mar. 28, 2019

Related U.S. Application Data

(62) Division of application No. 14/405,765, filed as application No. PCT/US2013/043839 on Jun. 3, 2013, now Pat. No. 10,190,180.

(60) Provisional application No. 61/655,382, filed on Jun. 4, 2012.

(51) Int. Cl.
*C12Q 1/70* (2006.01)

(52) U.S. Cl.
CPC ........ *C12Q 1/707* (2013.01); *C12Q 2531/113* (2013.01); *C12Q 2600/156* (2013.01); *C12Q 2600/16* (2013.01)

(58) Field of Classification Search
CPC .......................... C12Q 1/707; C12Q 2600/156
See application file for complete search history.

(56) References Cited

U.S. PATENT DOCUMENTS

| | | | |
|---|---|---|---|
| 10,190,180 B2 | 1/2019 | Pollner et al. | |
| 2003/0050470 A1 | 3/2003 | An et al. | |
| 2003/0152591 A1* | 8/2003 | Sablon ................ | C12Q 1/707 424/225.1 |
| 2005/0069870 A1* | 3/2005 | Sablon ................ | A61P 31/14 435/5 |
| 2005/0260567 A1* | 11/2005 | Orle ................... | C12Q 1/6883 435/5 |
| 2007/0172926 A1 | 7/2007 | Holland-Staley | |
| 2009/0047663 A1* | 2/2009 | Holland-Staley ...... | C12Q 1/707 435/5 |
| 2009/0186045 A1 | 7/2009 | Ray et al. | |
| 2012/0052482 A1* | 3/2012 | Opdyke ............... | C12Q 1/707 435/5 |

FOREIGN PATENT DOCUMENTS

| | | |
|---|---|---|
| EP | 1026262 A2 | 8/2000 |
| EP | 2236624 A1 | 10/2010 |
| EP | 2855710 B2 | 8/2017 |
| WO | WO 2002/083948 A1 | 10/2002 |
| WO | WO 2008/002165 A2 | 1/2008 |
| WO | WO 2009/023358 A2 | 2/2009 |
| WO | WO 2009/056966 A1 | 5/2009 |
| WO | WO 2013/184553 A1 | 12/2013 |

OTHER PUBLICATIONS

Gadberry MD, Malcomber ST, Doust AN, Kellogg EA. Primaclade—a flexible tool to find conserved PCR primers across multiple species. Bioinformatics. Apr. 1, 2005; 21(7):1263-4. Epub Nov. 11, 2004. (Year: 2004).*
Genbank Accession No. AJ000009—Hepatitis C virus complete genome sequence (submitted Jul. 2, 1997, retrieved on Dec. 4, 2020 from https://www.ncbi.nlm.nih.gov/nuccore/AJ000009). (Year: 1997).*
SantaLucia Jr, John. Physical principles and visual-OMP software for optimal PCR design. PCR Primer Design. Humana Press, 2007: pp. 3-33. (Year: 2007).*
Kuntzen et al. Naturally occurring dominant resistance mutations to hepatitis C virus protease and polymerase inhibitors in treatment-naïve patients. Hepatology.Dec. 2008; 48(6):1769-78. (Year: 2008).*
Rolfe, K.J., Wreghitt, T.G., Alexander, G.J. and Curran, M.D., 2009. A Real-Time Taqman® Method for Hepatitis C Virus Genotyping and Methods for Further Subtyping of Isolates. In Hepatitis C (pp. 55-71). Humana Press. (Year: 2009).*
Vicenti et al., 2012. Naturally occurring hepatitis C virus (HCV) NS3/4A protease inhibitor resistance-related mutations in HCV genotype 1-infected subjects in Italy. Journal of Antimicrobial Chemotherapy, 67(4), pp. 984-987. (Year: 2012).*
Chevaliez et al., "Hepatitis C Virus (HCV) Genotype 1 Subtype Identification in New HCV Drug Development and Future Clinical Practice," PLOS one, vol. 4, Issue 12, e8209, (Dec. 2009).
Database Geneseq [Online] Oct. 23, 2010 (Oct. 23, 2010), "HCV interfering RNA target/sense strand #4465.", retrieved from EBI accession No. GSN :BAG93582, Database accession No. BAG93582.
Database Geneseq [Online] Sep. 23, 2010 (Sep. 23, 2010), "HCV interfering RNA target/sense strand #5094.", retrieved from EBI accession No. GSN :BAG94211, Database accession No. BAG94211.
Database Geneseq [Online], Sep. 23, 2010 (Sep. 23, 2010), "HCV interfering RNA target/sense strand #7952," XP002712146, retrieved from EBI accession No. GSN:BAG97069, Database accession No. BAG97069 sequence.
Genbank Accession No. AF009606—Hepatitis C virus subtype 1a polyprotein gene, complete cds (submitted by Kolykhalov et al., Jun. 19, 1997, retrived on Sep. 22, 2017).
Genbank Accession No. AY003957—Hepatitis C virus isolate BD259 clone V non-structural protein 5b gene, partial cds (submitted by Harris Jun. 2000, retrieved on Sep. 25, 2017).

(Continued)

*Primary Examiner* — Teresa E Strzelecka
*Assistant Examiner* — Olayinka A Oyeyemi
(74) *Attorney, Agent, or Firm* — Alston & Bird LLP; Jeff Landes

(57) ABSTRACT

Disclosed are nucleic acid oligomers for amplifying one or more selected regions of HCV nucleic acid. Also disclosed are methods for specific amplification and characterization of HCV nucleic acid using the disclosed oligomers, as well as corresponding reaction mixtures and kits.

10 Claims, 10 Drawing Sheets

Specification includes a Sequence Listing.

(56) References Cited

OTHER PUBLICATIONS

Genbank Accession No. AY003965—Hepatitis C virus isolate BD268 cloane IV non-structural protein 5b gene, partial cds (submitted by Harris Jun. 2000, retrieved on Sep. 25, 2017).
Genbank Accession No. DQ10749—Hepatitis C virus genomic RNA, complete genome, isolate: HC-J1 (submitted by Okamoto Mar. 1992, retrieved on Sep. 25, 2017).
Genbank Asscession No. M62321—Hepatitis C virus subtype 1a, complete genonme (submitted Sep. 5, 2007, retrieved on Sep. 27, 2017).
International Preliminary Report on Patentability, International Application No. PCT/US2013/043839, dated Dec. 9, 2014.
International Search Report, International Application No. PCT/US2013/043839, dated Sep. 18, 2013.
Kutzen et al., "Naturally Occurring Dominant Resistance Mutations to Hepatitis C Virus Protease and Polymerase Inhibitors in Treatment-Naïve Patients," Hepatology, vol. 48, No. 6, pp. 1769-1778, (Dec. 2008).
Lowe, et al., "A computer program for selection of oligonucleotide primers for polymerase chain reactions," Nucleic Acids Res. 18(7): 1757-1761, (Apr. 11, 1990).
Patent Examination Report No. 1, Australian Patent Application No. 2013205064, dated Dec. 29, 2014.
Pickett et al., "Evidence for Separation of HCV Subtype 1a into Two Distinct Clades," J Viral Hepat., 18(9): 608-618, (Sep. 2011).
Rolfe et al., "Hepatitis C: Methods and Protocols," Second Edition, vol. 510, Humana Press: p. 55-71, (2009).
Santalucia Jr. et al. "Physical principles and visual—OMP software for optimal PCR design," PCR Primer Design, Humana Press, pp. 3-33, (2007).
U.S. Appl. No. 14/405,765, Final Office Action dated May 30, 2018.
U.S. Appl. No. 14/405,765, Notice of Allowance dated Sep. 6, 2018.
U.S. Appl. No. 14/405,765, Requirement for Restriction/Election dated Apr. 5, 2017.
Vicenti et al., "Naturally occurring hepatitis C virus (HCV) NS3/4A protease inhibitor resistance-related mutations in HCV genotype 1-infected subjects in Italy," J Antimicrob Chemother, 67(4):984-7, (2012).
Written Opinion of the International Searching Authority, International Application No. PCT/US2013/043839, dated Sep. 18, 2013.
U.S. Appl. No. 61/655,382, filed Jun. 4, 2012, Expired.
PCT/US2013/043839, Jun. 3, 2013, 2013/184553, Expired.
U.S. Appl. No. 14/405,765, filed Dec. 4, 2014, U.S. Pat. No. 10,190,180, Issued.

* cited by examiner

```
GCCAGCCCCCTGATGGGGGCGACACTCCACCATGAATCACTCCCCTGTGA
GGAACTACTGTCTTCACGCAGAAAGCGTCTAGCCATGGCGTTAGTATGAG
TGTCGTGCAGCCTCCAGGACCCCCCTCCCGGGAGAGCCATAGTGGTCTG
CGGAACCGGTGAGTACACCGGAATTGCCAGGACGACCGGGTCCTTTCTTG
GATAAACCCGCTCAATGCCTGGAGATTTGGGCGTGCCCCCGCAAGACTGC
TAGCCGAGTAGTGTTGGGTCGCGAAAGGCCTTGTGGTACTGCCTGATAGG
GTGCTTGCGAGTGCCCCGGGAGGTCTCGTAGACCGTGCACCATGAGCACG
AATCCTAAACCTCAAAGAAAAACCAAACGTAACACCAACCGTCGCCCACA
GGACGTCAAGTTCCCGGGTGGCGGTCAGATCGTTGGTGGAGTTTACTTGT
TGCCGCGCAGGGGCCCTAGATTGGGTGTGCGCGCGACGAGGAAGACTTCC
GAGCGGTCGCAACCTCGAGGTAGACGTCAGCCTATCCCCAAGGCACGTCG
GCCCGAGGGCAGGACCTGGGCTCAGCCCGGGTACCCTTGGCCCCTCTATG
GCAATGAGGGTTGCGGGTGGGCGGGATGGCTCCTGTCTCCCGTGGCTCT
CGGCCTAGCTGGGGCCCCACAGACCCCGGCGTAGGTCGCGCAATTTGGG
TAAGGTCATCGATACCCTTACGTGCGGCTTCGCCGACCTCATGGGGTACA
TACCGCTCGTCGGCGCCCTCTTGGAGGCGCTGCCAGGGCCCTGGCGCAT
GGCGTCCGGGTTCTGGAAGACGGCGTGAACTATGCAACAGGGAACCTTCC
TGGTTGCTCTTTCTCTATCTTCCTTCTGGCCCTGCTCTCTTGCCTGACTG
TGCCCGCTTCAGCCTACCAAGTGCGCAATTCCTCGGGGCTTTACCATGTC
ACCAATGATTGCCCTAACTCGAGTATTGTGTACGAGGCGGCCGATGCCAT
CCTGCACACTCCGGGGTGTGTCCCTTGCGTTCGCGAGGGTAACGCCTCGA
GGTGTTGGGTGGCGGTGACCCCACGGTGGCCACCAGGGACGGCAAACTC
CCCACAACGCAGCTTCGACGTCATATCGATCTGCTTGTCGGGAGCGCCAC
CCTCTGCTCGGCCCTCTACGTGGGGACCTGTGCGGGTCTGTCTTTCTTG
TTGGTCAACTGTTTACCTTCTCTCCCAGGCGCCACTGGACGACGCAAGAC
TGCAATTGTTCTATCTATCCCGGCCATATAACGGGTCATCGCATGGCATG
GGATATGATGATGAACTGGTCCCCTACGGCAGCGTTGGTGGTAGCTCAGC
TGCTCCGGATCCCACAAGCCATCATGGACATGATCGCTGGTGCTCACTGG
GGAGTCCTGGCGGGCATAGCGTATTTCTCCATGGTGGGGAACTGGGCGAA
GGTCCTGGTAGTGCTGCTGCTATTTGCCGGCGTCGACGCGGAAACCCACG
TCACCGGGGGAAGTGCCGGCCGCACCACGGCTGGGCTTGTTGGTCTCCTT
ACACCAGGCGCCAAGCAGAACATCCAACTGATCAACACCAACGGCAGTTG
GCACATCAATAGCACGGCCTTGAACTGCAATGAAAGCCTTAACACCGGCT
GGTTAGCAGGGCTCTTCTATCAGCACAAATTCAACTCTTCAGGCTGTCCT
GAGAGGTTGGCCAGCTGCCGACGCCTTACCGATTTTGCCCAGGGCTGGGG
TCCTATCAGTTATGCCAACGGAAGCGGCCTCGACGAACGCCCCTACTGCT
GGCACTACCCTCCAAGACCTTGTGGCATTGTGCCCGCAAAGAGCGTGTGT
GGCCCGGTATATTGCTTCACTCCCAGCCCCGTGGTGGTGGGAACGACCGA
```

Figure 1A

```
CAGGTCGGGCGCGCCTACCTACAGCTGGGGTGCAAATGATACGGATGTCT
TCGTCCTTAACAACACCAGGCCACCGCTGGGCAATTGGTTCGGTTGTACC
TGGATGAACTCAACTGGATTCACCAAAGTGTGCGGAGCGCCCCCTTGTGT
CATCGGAGGGGTGGGCAACAACACCTTGCTCTGCCCCACTGATTGTTTCC
GCAAGCATCCGGAAGCCACATACTCTCGGTGCGGCTCCGGTCCCTGGATT
ACACCCAGGTGCATGGTCGACTACCCGTATAGGCTTTGGCACTATCCTTG
TACCATCAATTACACCATATTCAAAGTCAGGATGTACGTGGGAGGGGTCG
AGCACAGGCTGGAAGCGGCCTGCAACTGGACGCGGGGCGAACGCTGTGAT
CTGGAAGACAGGGACAGGTCCGAGCTCAGCCCATTGCTGCTGTCCACCAC
ACAGTGGCAGGTCCTTCCGTGTTCTTTCACGACCCTGCCAGCCTTGTCCA
CCGGCCTCATCCACCTCCACCAGAACATTGTGGACGTGCAGTACTTGTAC
GGGGTAGGGTCAAGCATCGCGTCCTGGGCCATTAAGTGGGAGTACGTCGT
TCTCCTGTTCCTCCTGCTTGCAGACGCGCGCGTCTGCTCCTGCTTGTGGA
TGATGTTACTCATATCCCAAGCGGAGGCGGCTTTGGAGAACCTCGTAATA
CTCAATGCAGCATCCCTGGCCGGGACGCACGGTCTTGTGTCCTTCCTCGT
GTTCTTCTGCTTTGCGTGGTATCTGAAGGGTAGGTGGGTGCCCGGAGCGG
TCTACGCCTTCTACGGGATGTGGCCTCTCCTCCTGCTCCTGCTGGCGTTG
CCTCAGCGGGCATACGCACTGGACACGGAGGTGGCCGCGTCGTGTGGCGG
CGTTGTTCTTGTCGGGTTAATGGCGCTGACTCTGTCGCCATATTACAAGC
GCTACATCAGCTGGTGCATGTGGTGGCTTCAGTATTTTCTGACCAGAGTA
GAAGCGCAACTGCACGTGTGGGTTCCCCCCCTCAACGTCCGGGGGGGCG
CGATGCCGTCATCTTACTCATGTGTGTTGTACACCCGACTCTGGTATTTG
ACATCACCAAACTACTCCTGGCCATCTTCGGACCCCTTTGGATTCTTCAA
GCCAGTTTGCTTAAAGTCCCCTACTTCGTGCGCGTTCAAGGCCTTCTCCG
GATCTGCGCGCTAGCGCGGAAGATAGCCGGAGGTCATTACGTGCAAATGG
CCATCATCAAGTTAGGGGCGCTTACTGGCACCTATGTGTATAACCATCTC
ACCCCTCTTCGAGACTGGGCGCACAACGGCCTGCGAGATCTGGCCGTGGC
TGTGGAACCAGTCGTCTTCTCCCGAATGGAGACCAAGCTCATCACGTGGG
GGGCAGATACCGCCGCGTGCGGTGACATCATCAACGGCTTGCCCGTCTCT
GCCCGTAGGGGCCAGGAGATACTGCTTGGGCCAGCCGACGGAATGGTCTC
CAAGGGGTGGAGGTTGCTGGCGCCCATCACGGCGTACGCCCAGCAGACGA
GAGGCCTCCTAGGGTGTATAATCACCAGCCTGACTGGCCGGGACAAAAAC
CAAGTGGAGGGTGAGGTCCAGATCGTGTCAACTGCTACCCAAACCTTCCT
GGCAACGTGCATCAATGGGGTATGCTGGACTGTCTACCACGGGGCCGGAA
CGAGGACCATCGCATCACCCAAGGGTCCTGTCATCCAGATGTATACCAAT
GTGGACCAAGACCTTGTGGGCTGGCCCGCTCCTCAAGGTTCCCGCTCATT
GACACCCTGCACCTGCGGCTCCTCGGACCTTTACCTGGTCACGAGGCACG
CCGATGTCATTCCCGTGCGCCGGCGAGGTGATAGCAGGGGTAGCCTGCTT
TCGCCCCGGCCCATTTCCTACTTGAAAGGCTCCTCGGGGGGTCCGCTGTT
```

Figure 1B

```
GTGCCCCGCGGGACACGCCGTGGGCCTATTCAGGGCCGCGGTGTGCACCC
GTGGAGTGGCTAAGGCGGTGGACTTTATCCCTGTGGAGAACCTAGAGACA
ACCATGAGATCCCCGGTGTTCACGGACAACTCCTCTCCACCAGCAGTGCC
CCAGAGCTTCCAGGTGGCCCACCTGCATGCTCCCACCGGCAGCGGTAAGA
GCACCAAGGTCCCGGCTGCGTACGCAGCCCAGGGCTACAAGGTGTTGGTG
CTCAACCCCTCTGTTGCTGCAACGCTGGGCTTTGGTGCTTACATGTCCAA
GGCCCATGGGGTTGATCCTAATATCAGGACCGGGGTGAGAACAATTACCA
CTGGCAGCCCCATCACGTACTCCACCTACGGCAAGTTCCTTGCCGACGGC
GGGTGCTCAGGAGGTGCTTATGACATAATAATTTGTGACGAGTGCCACTC
CACGGATGCCACATCCATCTTGGGCATCGGCACTGTCCTTGACCAAGCAG
AGACTGCGGGGCGAGACTGGTTGTGCTCGCCACTGCTACCCCTCCGGGC
TCCGTCACTGTGTCCCATCCTAACATCGAGGAGGTTGCTCTGTCCACCAC
CGGAGAGATCCCTTTTTACGGCAAGGCTATCCCCCTCGAGGTGATCAAGG
GGGGAAGACATCTCATCTTCTGCCACTCAAAGAAGAAGTGCGACGAGCTC
GCCGCGAAGCTGGTCGCATTGGGCATCAATGCCGTGGCCTACTACCGCGG
TCTTGACGTGTCTGTCATCCCGACCAGCGGCGATGTTGTCGTCGTGTCGA
CCGATGCTCTCATGACTGGCTTTACCGGCGACTTCGACTCTGTGATAGAC
TGCAACACGTGTGTCACTCAGACAGTCGATTTCAGCCTTGACCCTACCTT
TACCATTGAGACAACCACGCTCCCCAGGATGCTGTCTCCAGGACTCAAC
GCCGGGGCAGGACTGGCAGGGGGAAGCCAGGCATCTACAGATTTGTGGCA
CCGGGGGAGCGCCCCTCCGGCATGTTCGACTCGTCCGTCCTCTGTGAGTG
CTATGACGCGGGCTGTGCTTGGTATGAGCTCACGCCCGCCGAGACTACAG
TTAGGCTACGAGCGTACATGAACACCCCGGGGCTTCCCGTGTGCCAGGAC
CATCTTGAATTTTGGGAGGGCGTCTTTACGGGCCTCACTCATATAGATGC
CCACTTTCTATCCCAGACAAAGCAGAGTGGGGAGAACTTTCCTTACCTGG
TAGCGTACCAAGCCACCGTGTGCGCTAGGGCTCAAGCCCCTCCCCCATCG
TGGGACCAGATGTGGAAGTGTTTGATCCGCCTTAAACCCACCCTCCATGG
GCCAACACCCCTGCTATACAGACTGGGCGCTGTTCAGAATGAAGTCACCC
TGACGCACCCAATCACCAAATACATCATGACATGCATGTCGGCCGACCTG
GAGGTCGTCACGAGCACCTGGGTGCTCGTTGGCGGCGTCCTGGCTGCTCT
GGCCGCGTATTGCCTGTCAACAGGCTGCGTGGTCATAGTGGGCAGGATTG
TCTTGTCCGGGAAGCCGGCAATTATACCTGACAGGGAGGTTCTCTACCAG
GAGTTCGATGAGATGGAAGAGTGCTCTCAGCACTTACCGTACATCGAGCA
AGGGATGATGCTCGCTGAGCAGTTCAAGCAGAAGGCCCTCGGCCTCCTGC
AGACCGCGTCCCGCCAAGCAGAGGTTATCACCCCTGCTGTCCAGACCAAC
TGGCAGAAACTCGAGGTCTTCTGGGCGAAGCACATGTGGAATTTCATCAG
TGGGATACAATACTTGGCGGGCCTGTCAACGCTGCCTGGTAACCCCGCCA
TTGCTTCATTGATGGCTTTTACAGCTGCCGTCACCAGCCCACTAACCACT
GGCCAAACCCTCCTCTTCAACATATTGGGGGGTGGGTGGCTGCCCAGCT
```

Figure 1C

```
CGCCGCCCCCGGTGCCGCTACCGCCTTTGTGGGCGCTGGCTTAGCTGGCG
CCGCCATCGGCAGCGTTGGACTGGGGAAGGTCCTCGTGGACATTCTTGCA
GGGTATGGCGCGGGCGTGGCGGGAGCTCTTGTAGCATTCAAGATCATGAG
CGGTGAGGTCCCCTCCACGGAGGACCTGGTCAATCTGCTGCCCGCCATCC
TCTCGCCTGGAGCCCTTGTAGTCGGTGTGGTCTGCGCAGCAATACTGCGC
CGGCACGTTGGCCCGGGCGAGGGGCAGTGCAATGGATGAACCGGCTAAT
AGCCTTCGCCTCCCGGGGGAACCATGTTTCCCCCACGCACTACGTGCCGG
AGAGCGATGCAGCCGCCCGCGTCACTGCCATACTCAGCAGCCTCACTGTA
ACCCAGCTCCTGAGGCGACTGCATCAGTGGATAAGCTCGGAGTGTACCAC
TCCATGCTCCGGTTCCTGGCTAAGGGACATCTGGGACTGGATATGCGAGG
TGCTGAGCGACTTTAAGACCTGGCTGAAAGCCAAGCTCATGCCACAACTG
CCTGGGATTCCCTTTGTGTCCTGCCAGCGCGGGTATAGGGGGGTCTGGCG
AGGAGACGGCATTATGCACACTCGCTGCCACTGTGGAGCTGAGATCACTG
GACATGTCAAAAACGGGACGATGAGGATCGTCGGTCCTAGGACCTGCAGG
AACATGTGGAGTGGGACGTTCCCCATTAACGCCTACACCACGGGCCCCTG
TACTCCCCTTCCTGCGCCGAACTATAAGTTCGCGCTGTGGAGGGTGTCTG
CAGAGGAATACGTGGAGATAAGGCGGGTGGGGGACTTCCACTACGTATCG
GGTATGACTACTGACAATCTTAAATGCCCGTGCCAGATCCCATCGCCCGA
ATTTTTCACAGAATTGGACGGGGTGCGCCTACATAGGTTTGCGCCCCCTT
GCAAGCCCTTGCTGCGGGAGGAGGTATCATTCAGAGTAGGACTCCACGAG
TACCCGGTGGGGTCGCAATTACCTTGCGAGCCCGAACCGGACGTAGCCGT
GTTGACGTCCATGCTCACTGATCCCTCCCATATAACAGCAGAGGCGGCCG
GGAGAAGGTTGGCGAGAGGGTCACCCCCTTCTATGGCCAGCTCCTCGGCC
AGCCAGCTGTCCGCTCCATCTCTCAAGGCAACTTGCACCGCCAACCATGA
CTCCCCTGACGCCGAGCTCATAGAGGCTAACCTCCTGTGGAGGCAGGAGA
TGGGCGGCAACATCACCAGGGTTGAGTCAGAGAACAAAGTGGTGATTCTG
GACTCCTTCGATCCGCTTGTGGCAGAGGAGGATGAGCGGGAGGTCTCCGT
ACCCGCAGAAATTCTGCGGAAGTCTCGGAGATTCGCCCGGGCCCTGCCCG
TTTGGGCGCGGCCGGACTACAACCCCCGCTAGTAGAGACGTGGAAAAAG
CCTGACTACGAACCACCTGTGGTCCATGGCTGCCCGCTACCACCTCCACG
GTCCCCTCCTGTGCCTCCGCCTCGGAAAAAGCGTACGGTGGTCCTCACCG
AATCAACCCTATCTACTGCCTTGGCCGAGCTTGCCACCAAAAGTTTTGGC
AGCTCCTCAACTTCCGGCATTACGGGCGACAATACGACAACATCCTCTGA
GCCCGCCCCTTCTGGCTGCCCCCCCGACTCCGACGTTGAGTCCTATTCTT
CCATGCCCCCCTGGAGGGGAGCCTGGGATCCGGATCTCAGCGACGGG
TCATGGTCGACGGTCAGTAGTGGGCCGACACGGAAGATGTCGTGTGCTG
CTCAATGTCTTATTCCTGGACAGGCGCACTCGTCACCCCGTGCGCTGCGG
AAGAACAAAAACTGCCCATCAACGCACTGAGCAACTCGTTGCTACGCCAT
CACAATCTGGTGTATTCCACCACTTCACGCAGTGCTTGCCAAAGGCAGAA
```

Figure 1D

```
GAAAGTCACATTTGACAGACTGCAAGTTCTGGACAGCCATTACCAGGACG
TGCTCAAGGAGGTCAAAGCAGCGGCGTCAAAAGTGAAGGCTAACTTGCTA
TCCGTAGAGGAAGCTTGCAGCCTGACGCCCCACATTCAGCCAAATCCAA
GTTTGGCTATGGGGCAAAAGACGTCCGTTGCCATGCCAGAAAGGCCGTAG
CCCACATCAACTCCGTGTGGAAAGACCTTCTGGAAGACAGTGTAACACCA
ATAGACACTACCATCATGGCCAAGAACGAGGTTTTCTGCGTTCAGCCTGA
GAAGGGGGGTCGTAAGCCAGCTCGTCTCATCGTGTTCCCCGACCTGGGCG
TGCGCGTGTGCGAGAAGATGGCCCTGTACGACGTGGTTAGCAAGCTCCCC
CTGGCCGTGATGGGAAGCTCCTACGGATTCCAATACTCACCAGGACAGCG
GGTTGAATTCCTCGTGCAAGCGTGGAAGTCCAAGAAGACCCCGATGGGGT
TCTCGTATGATACCCGCTGTTTTGACTCCACAGTCACTGAGAGCGACATC
CGTACGGAGGAGGCAATTTACCAATGTTGTGACCTGGACCCCAAGCCCG
CGTGGCCATCAAGTCCCTCACTGAGAGGCTTTATGTTGGGGGCCCTCTTA
CCAATTCAAGGGGGGAAAACTGCGGCTACCGCAGGTGCCGCGCGAGCGGC
GTACTGACAACTAGCTGTGGTAACACCCTCACTTGCTACATCAAGGCCCG
GGCAGCCTGTCGAGCCGCAGGGCTCCAGGACTGCACCATGCTCGTGTGTG
GCGACGACTTAGTCGTTATCTGTGAAAGTGCGGGGGTCCAGGAGGACGCG
GCGAGCCTGAGAGCCTTCACGGAGGCTATGACCAGGTACTCCGCCCCCCC
CGGGGACCCCCACAACCAGAATACGACTTGGAGCTTATAACATCATGCT
CCTCCAACGTGTCAGTCGCCCACGACGGCGCTGGAAAGAGGGTCTACTAC
CTTACCCGTGACCCTACAACCCCCTCGCGAGAGCCGCGTGGGAGACAGC
AAGACACACTCCAGTCAATTCCTGGCTAGGCAACATAATCATGTTTGCCC
CCACACTGTGGGCGAGGATGATACTGATGACCCATTTCTTTAGCGTCCTC
ATAGCCAGGGATCAGCTTGAACAGGCTCTTAACTGTGAGATCTACGGAGC
CTGCTACTCCATAGAACCACTGGATCTACCTCCAATCATTCAAAGACTCC
ATGGCCTCAGCGCATTTTCACTCCACAGTTACTCTCCAGGTGAAATCAAT
AGGGTGGCCGCATGCCTCAGAAAACTTGGGGTCCCGCCCTTGCGAGCTTG
GAGACACCGGGCCCGGAGCGTCCGCGCTAGGCTTCTGTCCAGAGGAGGCA
GGGCTGCCATATGTGGCAAGTACCTCTTCAACTGGGCAGTAAGAACAAAG
CTCAAACTCACTCCAATAGCGGCCGCTGGCCGGCTGGACTTGTCCGGTTG
GTTCACGGCTGGCTACAGCGGGGGAGACATTTATCACAGCGTGTCTCATG
CCCGGCCCCGCTGGTTCTGGTTTTGCCTACTCCTGCTCGCTGCAGGGGTA
GGCATCTACCTCCTCCCCAACCGATGAAGGTTGGGGTAAACACTCCGGCC
TCTTAGGCCATTTCCTGTTTTTTTTTTTTTTTTTTTTTTTTTTTTT
TTTTTTTTTTTTTTTCTTTTTTTTTTTTTTCCTTTTTTTTTTT
TTTTTTTCTTTCCTTCTTTTTCCTTTCTTTTCCTTCCTTCTTTAATGG
TGGCTCCATCTTAGCCCTAGTCACGGCTAGCTGTGAAGGTCCGTGAGCC
GCATGACTGCAGAGAGTGCTGATACTGGCCTCTCTGCAGATCATGT
```

Figure1E

```
GGCGACACTCCACCATAGATCACTCCCCTGTGAGGAACTACTGTCTTCAC
GCAGAAAGCGTCTAGCCATGGCGTTAGTATGAGTGTCGTGCAGCCTCCAG
GACCCCCCTCCCGGGAGAGCCATAGTGGTCTGCGGAACCGGTGAGTACA
CCGGAATTGCCAGGACGACCGGGTCCTTTCTTGGATCAACCCGCTCAATG
CCTGGAGATTTGGGCGTGCCCCCGCGAGACTGCTAGCCGAGTAGTGTTGG
GTCGCGAAAGGCCTTGTGGTACTGCCTGATAGGGTGCTTGCGAGTGCCCC
GGGAGGTCTCGTAGACCGTGCACCATGAGCACGAATCCTAAACCTCAAAG
AAAAACCAAACGTAACACCAACCGCCGTCCACAGGACGTCAAGTTCCCGG
GCGGTGGTCAGATCGTTGGTGGAGTTTACCTGTTGCCGCGCAGGGGCCCC
AGGTTGGGTGTGCGCGCGCTCAGGAAGACTTCCGAGCGGTCGCAACCTCG
TGGAAGGCGACAACCTATCCCCAAGGCTCGCCGACCCGAGGGCAGGGCCT
GGGCTCAGCCCGGGTACCCTTGGCCCCTCTATGGCAATGAGGGCATGGGG
TGGGCAGGATGGCTCCTGTCACCCCGTGGTTCTCGGCCTAGTTGGGGCCC
CTCAGACCCCGGCGTAGGTCGCGTAATTTGGGTAAGGTCATCGATACCC
TTACATGCGGCTTCGCCGACCTCATGGGGTACATTCCGCTCGTCGGCGCC
CCTCTAGGGGCGCCGCCAGGGCCTGGCGCATGGCGTCCGGGTTCTGGA
GGACGGCGTGAACTATGCAACAGGGAATTTGCCCGGTTGCTCTTTCTCTA
TCTTCCTCTTGGGTTTGCTGTCTTGTTTGACCATCCCAGCTTCCGCTTAT
GAAGTGCGCAACGTGTCCGGGGTGTACCATGTCACGAACGACTGCTCCAA
CGCAAGCATTGTGTATGAGGCAGCGGACATGATCATGCACGTCCCCGGGT
GCGTGCCCTGCGTTCGGGTGGACAACTCCTCCCGTTGCTGGGTAGCGCTC
ACCCCCACGCTTGCGGCCAGGAACGCTAGCGTCCCTACTACGGCAATACG
ACGCCACGTCGATTTGCTCGTTGGGGCGGCTACTTTCTGTTCCGCTATGT
ACGTGGGGATCTCTGCGGATCTGTTTTCCTCGTCGCCCAGCTGTTCACC
TTCTCGCCCCGCCGGCATGAGACGGTACAGGACTGCAATTGTTCAATCTA
TCCCGGCCACATAACGGGTCACCGCATGGCTTGGGATATGATGATGAACT
GGTCACCCACAGCAGCCCTAGTCGTATCGCAGTTACTCCGGATCCCACAA
GCTATCGTGGATATGGTGGCGGGGCCCACTGGGGAGTCCTGGCGGGCCT
CGCCTACTATTCCATGGTGGGGAACTGGGCTAAGGTTTTGATTGTGATGC
TACTCTTTGCCGGCGTTGACGGGGACACCCACACGACGGGGGGGTGGCG
GGCCGCGACACGCTGCGCTTCACGGGGTTCTTTTCATTGGGGCCGAAACA
AAAGATCCAGCTTGTAAACACCAACGGCAGCTGGCACATCAACAGGACTG
CCCTGAACTGCAATGACTCCCTCAACACTGGGTGGCTCGCCGCGCTGTTC
TACACACACAGCTTCAACGCGTCTGGATGCCCAGAGCGGATGGCCAGCTG
CCACCCCATCGACGAGTTCGCTCAGGGGTGGGGTCCCATTACTTACGCTG
AACATAGCAGCTCGGACCAGAGGCCCTACTGTTGGCACTACGCACCTCAG
CCGTGCGGTATTGTACCCGCGTCGGAGGTGTGTGGTCCAGTGTATTGCTT
CACCCCAAGCCCTGTTGTGGTGGGACAACCGATCGTCACGGCGTCCCTA
CGTATAGCTGGGGGGAGAATGGGACGGACGTGCTGCTTCTCAACAACACG
```

Figure 2A

```
CGGCCGCCGCAAGGCAACTGGTTCGGCTGTACATGGATGAACGGCACTGG
GTTCACCAAGACGTGCGGGGGCCCCCGTGTAACATCGGGGGGGTCGGCA
ACAACACCCTGACCTGCCCCACGGACTGCTTCCGGAAGCACCCCGAGGCC
ACTTACACCAAATGCGGCTCGGGGCCTTGGTTGACACCTAGGTGCATGGT
TGACTACCCATACAGGCTCTGGCACTACCCCTGCACTGTCAACTTCACCA
TCTTTAAGGTTAGGATGTATGTGGGGGGCGTGGAACACAGGCTCAGCGCC
GCATGCAATTGGACTCGAGGAGAGCGTTGTGACCTGGAGGACAGGGATAG
ATCAGAGCTTAGCCCGCTGCTGCTGTCCACAACAGAGTGGCAGGTGCTGC
CCTGTTCCTTCACCACCCTACCGGCTCTGTCCACTGGTTTGATCCATCTC
CACCAGAACATCGTGGACGTGCAATACTTGTACGGTATAGGGTCGGTGGT
TGTCTCCTTTGCAATCAAATGGGAGTATGTCGTGTTGCTCTTCCTTCTCC
TGGCAGACGCGCGCGTCTGTGCCTGCTTGTGGATGATGCTGCTGATAGCC
CAAGCTGAGGCCGCCTTAGAGAACCTGGTGGTCCTCAATGCAGCGTCCGT
GGCCGGAGCACATGGCATTCTCTCCTTCCTTGTGTTTTTCTGTGCTGCCT
GGTACATCAAGGGCAGGCTGGTCCCTGGAGCGGCATATGCTATCTATGGC
GTATGGCCGCTACTCCTGCTCCTGCTGGCGCTACCACCACGGGCATACGC
CTTGGACCGGGAGATGGCTGCATCGTGCGGAGGCGCGGTTTTCGTAGGTC
TGGTACTCTTGACCTTGTCACCACACTATAAAGAGTTCCTCGCCAGGCTT
ATATGGTGGTTGCAATACTACATCACCAGAGCCGAGGCGCTACTGCAAGT
GTGGATCCCCCCCCTCAATGTTCGGGGGGCCGCGACGCCATCATCCTCC
TCACGTGTGTGGTCCACCCAGAGCTAATTTTTGACATCACCAAGCTCTTG
CTCGCCATGCTCGGCCCGCCCATGGTGCTCCAGGCTGTCATAACCAAGGT
GCCGTACTTTGTGCGCGCTCAAGGGCTCATTCGTGCATGCATGTTGGTGC
GGAAAGTCGCTGGGGGCCATTACGTCCAAATGGCTCTCATGAAGCTGGCC
GGGTTGACAAGCACGTACGTTTATGACCATCTTACTCCGTTGCAGGACTG
GGCCCACGGCGGCCTACGAGACCTCGCGGTGGCAGTTGAGCCCGTTGTTT
TTTCTGACATGGAGACCAAGATCATCACCTGGGGGCGGACACTGCGGCG
TGTGGTGACATCATCTCGGGGTTACCTGTCTCCGCCCGAAGGGGGAGGGA
GATACTCCTGGGACCGGCCGATAGTCTTAAAGAGCAGGGATGGCGACTCC
TTGCACCCATCACGGCTTACTCCCAACAGACGCGGGGCCTACTTGGTTGC
ATCATCACTAGCCTCACAGGCCGGGACAAGAACCAGGTCGAGGGGGAGGT
TCAAGTGGTCTCCACCGCAACACAATCTTTCCTGGCGACCTGTGTCAACG
GCGTGTGTTGGACTGTGTATCATGGCGCCGGCTCAAAGACCCTAGCCGGC
CCAAAAGGTCCAGTCACCCAAATGTACACCAATGTAGACCAGGACCTCGT
CGGCTGGCCCGCGCCCCCGGGGCGCGTTCCTTGACACCATGCACCTGTG
GCAGCTCGGACCTTTACTTGGTCACGAGACATGCCGATGTCATCCCGGTG
CGCCGGCGGGGCGACAGCAGGGGAAGCCTACTCTCCCCAGGCCCGTCTC
CTACTTGAAGGGCTCTTCGGGTGGTCCATTGCTCTGCCCCTCGGGGCACG
CTGTGGGCATCTTCCGGCTGCTGTGTGCACCCGGGGGTCGCGAAGGCG
GTGGACTTTGTGCCCGTTGAGTCTATGGAAACTACTATGCGGTCTCCGGT
CTTCACGGACAATTCATCTCCCCGGCCGTACCGGAGACATTCCAGGTGG
```

Figure 2B

```
CCCATCTACACGCTCCCACCGGTAGCGGCAAGAGCACTAAGGTGCCGGCT
GCATATGCAGCTCAAGGGTACAAGGTACTCGTCCTGAACCCGTCCGTTGC
CGCCACCCTGGGCTTTGGGGCGTACATGTCCAAGGCACATGGTACCGACC
CCAACATCAGAACTGGGGTAAGGACCATCACCACGGGCGCTCCCATTACG
TACTCCACCTATGGCAAGTTCCTCGCCGATGGTGGTTGTTCTGGGGGCGC
CTATGACATTATAATATGTGATGAGTGCCACTCAACTGACTCGACTACCA
TCCTGGGCATTGGCACAGTCCTGGACCAAGCGGAGACGGCTGGAGCACGG
CTCGTCGTGCTCGCCACCGCTACGCCTCCGGGATCGGTCACCGTGCCGCA
TCCCAACATCGAGGAGGTGGCCCTGTCCAACATTGGAGAGATCCCCTTCT
ATGGCAAAGCCATCCCCATTGAAACCATCAAGGGGGGAAGACACCTCATT
TTCTGCCATTCCAAGAAGAAGTGTGACGAGCTCGCTGCAAAGCTGTCGGG
CCTCGGACTCAACGCTGTAGCGTATTACCGGGGCCTTGACGTGTCCGTCA
TACCGACCAGCGGAGACGTCGTTGTCGTAGCAACAGACGCTCTAATGACG
GGCTTTACCGGCGACTTTGACTCAGTGATCGACTGTAACACATGTGTCAC
CCAAACAGTCGATTTCAGCTTGGACCCTACCTTCACCATTGAGACGACGA
CCGTGCCCCAAGACGCAGTGTCGCGCTCGCAACGGCGAGGCAGGACTGGT
AGGGGCAGGAGAGGCATCTACAGGTTTGTGACTCCGGGAGAGCGGCCCTC
GGGCATGTTCGATTCCTCGGTCCTGTGTGAGTGCTATGACGCGGGCTGTG
CTTGGTATGAGCTCACGCCCGCCGAGACTTCGGTTAGGTTGCGGGCTTAC
CTAAACACACCAGGGTTGCCCGTCTGCCAAGACCACCTGGAGTTCTGGGA
GAGCGTCTTCACAGGCCTCACCCACATAGACGCCCACTTCTTGTCCCAGA
CCAAACAAGCGGGAGAGAACTTCCCCTACCTGACAGCGTACCAGGCCACA
GTGTGTGCCAGGGCTCAGGCTCCACCTCCATCGTGGGATCAAATGTGGAA
GTGTCTCATACGGCTAAAGCCTACGCTGCACGGGCCAACACCCCTGCTGT
ATAGGCTAGGAGCCGTCCAAAACGAGGTCGTCCTTACACACCCCATAACC
AAATACATCATGGCATGCATGTCGGCTGACCTAGAGGTCGTCACGAGCAC
CTGGGTGCTAGTGGGCGGAGTCCTCGCAGCCCTGGCTGCGTATTGCCTGA
CAACGGGCAGCGTGGTCATTGTGGGCAGGATTATCTTGTCCGGGAGGCCG
GCTATCATTCCCGACAGGGAAGTCCTTTACCAGGAGTTCGATGAGATGGA
AGAGTGCGCCTCACACCTTCCTTACATCGAACAGGGAATGCAGCTCGCCG
AACAATTCAAACAGAAGGCGCTCGGGTTGCTGCAGACAGCCACTAAGCAA
GCGGAGGCTGCTGTTCCCGTGGTGGAATCCAAGTGGCAAGCCCTTGAGGC
TTTTTGGGCGAAGCACATGTGGAACTTCATCAGCGGGATACAGTACTTAG
CAGGCTTGTCCACTCTGCCTGGGAACCTCGCAATAGCATCACTGATGGCA
TTCACAGCCTCCATCACCAGCCCGCTCACCACCCAACATACCCTCCTGTT
TAACATCTTGGGGGGATGGGTGGCTGCCCAACTCGCTCCCCCCAGCGCCG
CCTCAGCTTTCGTAGGCGCCGGCATCGCCGGTGCGGCCGTTGGCAGCATA
GGCCTTGGGAAGGTGCTTGTGGACATCCTGGCGGGCTATGGAGCAGGAGT
GGCTGGCGCGCTCGTGGCCTTTAAAGTCATGAGCGGCGAGATGCCCTCCA
CCGAGGACCTGGTCAACTTACTCCCTGCCATCCTCTCTCCTGGCGCCCTG
GTCGTCGGGGTCGTGTGCGCAGCAATACTGCGTCGGCATGTGGGCCCTGG
```

Figure2C

```
GGAGGGGGCTGTGCAGTGGATGAACCGGCTGATAGCGTTCGCTTCGCGGG
GTAACCACGTGTCCCCCACGCACTATGTGCCTGAGAGCGACGCCGCAGCG
CGTGTCACTCAGATCCTCTCCAGCCTTACCATCACCCAGCTGTTGAAGAG
GCTCCACCAGTGGATTAACGAGGACTGCTCCACGCCATGCTCCGGTTCGT
GGCTAAGGGATGTTTGGGACTGGATATGCACGGTGTTGACTGACTTCAAG
ACCTGGCTCCAGTCCAAGCTCCTGCCACGGTTACCGGGAATCCCTTTTTA
CTCATGCCAGCGTGGGTACAAGGGAGTATGGCGGGGAGACGGCATCATGC
AAACCACCTGCCCATGTGGAGCACAGATCACTGGACATGTCAAAAACGGT
TCCATGAGGATCGTTGGGCCTAAAACCTGCAGCAACACGTGGCACGGAAC
ATTCCCCATCAACGCATACACCACGGGCCCCTGCACACCCTCCCCGGCGC
CAAACTATTCTAGGGCGCTGTGGCGGGTGGCTGCTGAGGAGTATGTGGAG
GTTACGCGGGTGGGGATTTCCACTACGTGACGGGCATGACCACTGACAA
CGTAAAATGCCCATGCCAGGTTCCGGCTCCCGAATTCTTCACGGAGGTGG
ATGGGGTGCGGCTGCACAGGTACGCCCCGGCGTGCAAACCCCTCCTACGG
GATGAAGTCACATTCCAGGTCGGGCTCAACCAATACGTGGTTGGGTCACA
ACTCCCATGCGAGCCCGAACCGGATGTAGTGGTGGTCACTTCCATGCTTA
CCGACCCCTCCCACATTACAGCAGAGACGGCTAAGCGTAGGCTGGACAGG
GGGTCTCCCCCCTCCTTGGCCAGCTCTTCAGCTAGCCAGTTGTCTGCGCC
TTCCTTGAAGGCGACATGCACTACCCGTCACGACTCCCAGACGCTGACC
TCATTGAGGCCAACCTCCTGTGGCGGCAGGAGATGGGCGGAAACATCACC
CGCGTGGAGTCTGAAAACAAGGTAGTAATTCTGGACTCTTTCGACCCGCT
TCGAGCGGAGGAGGATGAGAGGGAAGTATCCGTCGCGGCGGAGATTCTGC
GGAAATCCAGGAGATTCCCCCGAGCGATGCCCATATGGGCACGGCCGGAT
TACAACCCCCCACTGCTAGAGTCCTGGAAGGATCCGGACTACGTCCCTCC
GGTGGTGCACGGGTGCCCATTACCACCTACCAAGGCCCCTCCAATACCAC
CTCCACGGAAAAAGAGGACGGTTGTCCTGACAGAGTCCACCGTGTCTTCT
GCCTTGGCGGAGCTTGCTACAAAGACCTTCGGCAGCTCCGAATCGTCGGC
CGTCGACAGCGGCACGGCGACCGCCCCTCCTGACCAGCCCCCCGACAACG
ACGACACAGGATCCGACGTTGAATCGTGCTCCTCCATGCCCCCCCTTGAG
GGGGAGCCGGGGGATCCCGATCTCAGCGACGGGTCTTGGTCTACCGTGAG
CGAGGAGGCTAGTGAGGACGTCGTCTGCTGTTCGATGTCCTACACGTGGA
CGGGCGCTCTGATCACACCATGCGCCGCGGAAGAAAGCAAGCTGCCCATC
AATGCGTTGAGCAACTCTTTGCTGCGTCATCACAACATGGTGTACGCCAC
AACCTCCCGCAGCGCAAGCCAGCGGCAGAAGAAGGTCACTTTTGACAGAC
TGCAAGTCCTGGACGACCACTACCGGGACGTGCTCAAGGAGATGAAGGCG
AAGGCGTCCACAGTTAAGGCTAAACTTCTATCCGTAGAAGAAGCCTGCAA
GCTGACACCCCACATTCGGCCAGATCTAAATTTGGCTACGGGGCGAAGG
ACGTCCGGAACCTATCCAGCAAGGCCGTTAACCACATCCGCTCCGTGTGG
AAGGACTTGCTGGAAGACACTGAAACACCAATTGATACTACCATCATGGC
AAAGAATGAGGTCTTCTGCGTCCAACCAGAAAAAGGAGGCCGCAAGCCAG
CTCGCCTTATCGTGTTCCCAGACTTGGGGGTGCGCGTATGCGAGAAGATG
```

Figure2D

```
GCTCTTTATGACGTGGTCTCCACCCTTCCTCAGGCCGTGATGGGCCCCTC
GTACGGATTTCAGTACTCTCCTGGACAGCGGGTCGAGTTCCTGGTAAATG
CCTGGAAATCAAAGAAGTGTCCTATGGGCTTCGCATATGACACCCGCTGT
TTTGACTCAACGGTCACTGAGAGTGACATCCGTGTTGAGGAGTCAATTTA
CCAATGTTGTGACTTGGCCCCCGAAGCCAGACAGGCCATAAAGTCGCTCA
CAGAGCGGCTTTACATCGGGGGTCCCCTGACTAATTCAAAAGGGCAGAAC
TGCGGTTATCGCCGATGCCGCGCAAGCGGCGTGCTGACGACTAGCTGCGG
TAATACCCTTACATGTTACTTGAAGGCCTCTGCGGCCTGTCGAGCTGCAA
AGCTCCAGGACTGCACGATGCTCGTGTGCGGAGACGACCTCGTCGTTATC
TGTGAAAGCGCGGGAACCCAAGAGGACGCGGCGAGCCTACGAGTCTTCAC
GGAGGCCATGACTAGGTACTCTGCCCCCCCGGGGACCCGCCCCAACCAG
AATACGACCTGGAGCTGATAACATCATGCTCCTCGAATGTGTCGGTCGCG
CACGATGCATCCGGCAAGAGAGTATACTACCTCACCCGTGACCCCACCAC
CCCCCTTGCGCGGGCTGCGTGGGAGACAGCTAGACACACTCCAGTTAACT
CCTGGCTAGGCAACATCATCATGTATGCGCCCACTTTGTGGGCGAGGATG
ATTCTGATGACACACTTCTTCTCCATCCTTCTAGCTCAGGAACAACTTGA
AAAAGCCCTAGATTGTCAGATCTACGGGGCCTGTTACTCCATAGAGCCAC
TTGACCTACCTCAAATCATTCAGCGACTCCATGGTCTTAGCGCATTTTCA
CTCCACAGTTACTCCCCAGGTGAGATCAATAGGGTGGCTTCATGCCTCAG
GAAACTTGGGGTACCGCCCTTGCGAGCCTGGAGACATCGGGCCAGAAGTG
TCCGCGCTAAGCTACTGTCCCAGGGGGGAAGGGCTGCCACTTGTGGCCGC
TACCTCTTCAACTGGGCAGTAAAGACCAAACTTAAACTCACTCCAATTCC
GGCTGCGTCCCAGTTGGACTTGTCCAACTGGTTCGTTGCTGGTTACAGCG
GGGGAGACATATATCACAGCCTGTCTCGTGCCCGACCCCGCTGGTTCATG
TGGTGCCTACTCCTACTTTCTGTAGGGGTAGGCATCTACCTGCTCCCCAA
CCGATGAACGGGGAGCTAACCACTCCAGG
```

Figure2E

COMPOSITIONS AND METHODS FOR AMPLIFYING AND CHARACTERIZING HCV NUCLEIC ACID

CROSS-REFERENCE TO RELATED APPLICATIONS

This application is a divisional of U.S. patent application Ser. No. 14/405,765 filed Dec. 4, 2014, which is a national stage entry of PCT/US2013/043839 filed Jun. 3, 2013, which claims priority to U.S. Provisional Application No. 61/655,382 filed Jun. 4, 2012; each of which is incorporated herein by reference in its entirety for all purposes.

REFERENCE TO SEQUENCE LISTING

This application includes an electronic sequence listing in a file named 487933 DIV_SEQLST.TXT, created Dec. 6, 2018 and containing 60,464 bytes, which is hereby incorporated by reference in its entirety for all purposes.

BACKGROUND OF THE INVENTION

Hepatitis C Virus (HCV), the major cause of post-transfusion, community-acquired and cryptogenic non-A, non-B hepatitis (NANBH) (Choo et al., *Br. Med. Bull.* 46:423-441, 1990), is a persistent health threat worldwide, with more than one million new cases reported annually (Zein, *Clin. Micro. Rev.* 13:223-235, 2000). Over 170 million individuals are infected with HCV worldwide (see, e.g., Chevaliez et al., *PLoS ONE* 4:e8209, 2009.), and HCV infection is almost always chronic and persistent. The most severe consequences of HCV infection are chronic liver disease and death, and HCV infection is the primary impetus for liver transplantation in the United States (Zein, supra).

HCV is a positive strand single-stranded RNA virus approximately 10 kb long belonging to the Flaviviridae family (Zein, supra). There is considerable heterogeneity among isolates found in different geographic regions. These differences have been classified into multiple genotypes and subtypes. Although various different criteria have been used to characterize these genotypes, two principal modes of classification have been adopted. The more widely used of these was created by Peter Simmonds and uses Arabic numerals to denote different genotypes and latin letters for subtypes, e.g., type 1a, 1b, 2a, etc. (reviewed in Simmonds, *Hepatol.*, 21:570-83, 1995; Simmonds, *Hepatol.* 31 Suppl 1:54-60, 1999). According to this system, genotypes 1-3 are the prevalent types found in North America, Europe, and Japan, and the remaining types are found at various frequencies in parts of Asia and Africa. Thus in some instances HCV genotype may be of epidemiological importance, for example in determining the etiology of infection.

Efforts have been undertaken to elucidate the clinical significance of different genotypes. Some studies suggest that infections of type 1, in particular type 1b, may be associated with more severe disease and earlier recurrence (Zein et al., *Liver Transplant. Surg.* 1:354-357, 1995; Gordon et al., *Transplantation* 63:1419-1423, 1997). Certain studies have also indicated that genotypes other than type 1 may respond more favorably to various treatments, e.g. interferon (McHutchison et al., *N. Engl. J. Med.*, 339:1485-1492, 1998). It has been suggested that determination of HCV genotype in combination with other diagnostic markers, such as viral load, may be of value in arriving at disease prognoses (Zein, supra), and determining the course of treatment (National Institutes of Health Consensus Development Conference Statement; Management of Hepatitis C: 2002; Jun. 10-11, 2002).

Although HCV genotype 1 is generally considered as a homogeneous group, there are biological differences between the different subtypes of HCV genotype 1, which are related to differences in their nucleotide and amino acid sequences. For example, differences between subtype 1a and 1b (by far the most frequently encountered genotype 1 subtypes in clinical practice) include different efficacies of antiviral drugs and different resistance profiles to such drugs. (Chevaliez et al., *PLoS ONE* 4:e8209, 2009.) Several HCV inhibitors appear to have selective activity against different HCV genotype 1 subtypes, both in vitro and in vivo. (Id.) For example, differences have been observed in vitro with NS3/4A protease inhibitors, non-nucleoside inhibitors of HCV RdRp, and NS5A inhibitors (Erhardt et al., *Antivir. Ther.* 14:23-32, 2009; Jiang et al., *J. Hepatol.* 50 (suppl. 1):S6, 2009; Liang et al., *Gastroenterology* 135:1710-1718, 2008; Nettles et al., *Hepatology* 48 (suppl. 1): 1025A, 2008; Thompson et al., *J. Hepatol.* 50 (suppl. 1):S37, 2009).

Correct identification of HCV subtypes 1a and 1b is critical in clinical trials assessing new HCV drugs in order to correctly stratify and interpret efficacy and resistance data. In addition, such genotype identification is likely to become increasingly important in clinical practice to select HCV inhibitor treatment according to HCV genotype 1 subtype. (See Chevaliez et al., supra.)

Accordingly, there is a need for compositions and methods for determining genotype information for HCV type 1 so as to correctly identify mutations or single nucleotide polymorphisms (SNPs) associated with treatment efficacy or resistance, including the correct identification of HCV subtypes 1a and 1b. The present invention meets these and other needs.

SUMMARY OF THE INVENTION

In one aspect, the present invention provides a method for determining at least partial genotype information for hepatitis C virus type 1a (HCV-1a) or type 1b (HCV-1b) in a sample. The method generally includes the following steps: (1) contacting a sample, which is suspected of containing HCV-1a or HCV-1b viral RNA, with at least two amplification oligomers for amplifying at least one target region of an HCV-1a or HCV-1b target nucleic acid; (2) performing at least one in vitro nucleic acid amplification reaction (e.g., one or more of an RT-PCR amplification reaction, a PCR amplification reaction, and a transcription-mediated amplification (TMA) reaction), wherein any HCV-1a or HCV-1b target nucleic acid present in the sample is used as a template for generating at least one amplification product corresponding to the at least one target region; and (3) detecting the nucleobase at one or more nucleotide positions within the at least one amplification product, thereby determining at least partial genotype information for the HCV-1a or HCV-1b in the sample. In certain variations, the method further includes contacting the sample with at least one capture probe oligomer comprising a nucleotide sequence that hybridizes to the HCV-1a or HCV-1b target nucleic acid, wherein the at least one capture probe further comprises a nucleotide sequence or moiety that binds to an immobilized probe.

In some embodiments of a method for determining HCV-1a genotype information, the at least one target region and corresponding amplification oligomers are selected from the following:

(a) a first target region corresponding to nucleotide positions 8522 to 9372 of SEQ ID NO:155, wherein if the first target region is amplified, then the at least two amplification oligomers comprise (i) at least one oligomer comprising a target-hybridizing sequence substantially corresponding to a nucleotide sequence selected from SEQ ID NOs: 65, 43, and 34; and (ii) at least one oligomer comprising a target-hybridizing sequence substantially corresponding to a nucleotide sequence selected from SEQ ID NOs: 69, 38, and 41;

(b) a second target region corresponding to nucleotide positions 7788 to 8838 of SEQ ID NO: 155, wherein if the second target region is amplified, then the at least two amplification oligomers comprise (i) at least one oligomer comprising a target-hybridizing sequence substantially corresponding to a nucleotide sequence selected from SEQ ID NOs: 57, 63, and 28; and (ii) at least one oligomer comprising a target-hybridizing sequence substantially corresponding to a nucleotide sequence selected from SEQ ID NOs: 40, 35, and 42;

(c) a third target region corresponding to nucleotide positions 6966 to 7970 of SEQ ID NO:155, wherein if the third target region is amplified, then the at least two amplification oligomers comprise (i) at least one oligomer comprising a target-hybridizing sequence substantially corresponding to a nucleotide sequence selected from SEQ ID NOs: 60, 58, and 36; and (ii) at least one oligomer comprising a target-hybridizing sequence substantially corresponding to a nucleotide sequence selected from SEQ ID NOs: 31, 73, and 62;

(d) a fourth target region corresponding to nucleotide positions 6076 to 7117 of SEQ ID NO:155, wherein if the fourth target region is amplified, then the at least two amplification oligomers comprise (i) at least one oligomer comprising a target-hybridizing sequence substantially corresponding to a nucleotide sequence selected from SEQ ID NOs: 55, 70, and 29; and (ii) at least one oligomer comprising a target-hybridizing sequence substantially corresponding to a nucleotide sequence selected from SEQ ID NOs: 46, 45, and 61;

(e) a fifth target region corresponding to nucleotide positions 5094 to 6304 of SEQ ID NO:155, wherein if the fifth target region is amplified, then the at least two amplification oligomers comprise (i) at least one oligomer comprising a target-hybridizing sequence substantially corresponding to a nucleotide sequence selected from SEQ ID NOs: 39, 44, and 68; and (ii) at least one oligomer comprising a target-hybridizing sequence substantially corresponding to a nucleotide sequence selected from SEQ ID NOs: 47, 51, and 59;

(f) a sixth target region corresponding to nucleotide positions 4258 to 5297 of SEQ ID NO:155, wherein if the sixth target region is amplified, then the at least two amplification oligomers comprise (i) at least one oligomer comprising a target-hybridizing sequence substantially corresponding to a nucleotide sequence selected from SEQ ID NOs: 52, 49, and 72; and (ii) at least one oligomer comprising a target-hybridizing sequence substantially corresponding to a nucleotide sequence selected from SEQ ID NOs: 37, 75, and 53; and (g) a seventh target region corresponding to nucleotide positions 3434 to 4482 of SEQ ID NO:155, wherein if the seventh target region is amplified, then the at least two amplification oligomers comprise (i) at least one oligomer comprising a target-hybridizing sequence substantially corresponding to a nucleotide sequence selected from SEQ ID NOs: 77, 79, and 81; and (ii) at least one oligomer comprising a target-hybridizing sequence substantially corresponding to a nucleotide sequence selected from SEQ ID NOs: 78, 80, and 71.

In more particular embodiments of the method for determining HCV-1a genotype information as above, the at least one amplification oligomer of one or more of (a)(i), (a)(ii), (b)(i), (b)(ii), (c)(i), (c)(ii), (d)(i), (d)(ii), (e)(i), (e)(ii), (f)(i), (f)(ii), (g)(i), and (g)(ii) comprises or consists of the specified nucleotide sequence.

In certain variations of the method for determining HCV-1a genotype information, each of the first through seventh target regions of (a) through (g) are amplified to produce at least one amplification product corresponding to each of the HCV-1a target regions, and the detecting step comprises detecting the nucleobase at one or more positions within each of the seven amplification products. In some such variations, the contacting step includes contacting the sample with each of the oligomers of (a)(i); each of the oligomers of (a)(ii); each of the oligomers of (b)(i); each of the oligomers of (b)(ii); each of the oligomers of (c)(i); each of the oligomers of (c)(ii); each of the oligomers of (d)(i); each of the oligomers of (d)(ii); each of the oligomers of (e)(i); each of the oligomers of (e)(ii); each of the oligomers of (f)(i); each of the oligomers of (f)(ii); each of the oligomers of (g)(i); and each of the oligomers of (g)(ii).

In some embodiments of a method for determining HCV-1b genotype information, the at least one target region and corresponding amplification oligomers are selected from the following:

(a) a first target region corresponding to nucleotide positions 8504 to 9350 of SEQ ID NO: 156, wherein if the first target region is amplified, then the at least two amplification oligomers comprise (i) at least one oligomer comprising a target-hybridizing sequence substantially corresponding to a nucleotide sequence selected from SEQ ID NOs: 21, 86, and 88; and (ii) at least one oligomer comprising a target-hybridizing sequence substantially corresponding to a nucleotide sequence selected from SEQ ID NOs: 76, 87, and 89;

(b) a second target region corresponding to nucleotide positions 7771 to 8618 of SEQ ID NO:156, wherein if the second target region is amplified, then the at least two amplification oligomers comprise (i) at least one oligomer comprising a target-hybridizing sequence substantially corresponding to a nucleotide sequence selected from SEQ ID NOs: 82, 4, and 2; and (ii) at least one oligomer comprising a target-hybridizing sequence substantially corresponding to a nucleotide sequence selected from SEQ ID NOs: 90, 92, and 91;

(c) a third target region corresponding to nucleotide positions 6956 to 7966 of SEQ ID NO:156, wherein if the third target region is amplified, then the at least two amplification oligomers comprise (i) at least one oligomer comprising a target-hybridizing sequence substantially corresponding to a nucleotide sequence selected from SEQ ID NOs: 83, 24, and 94; and (ii) at least one oligomer comprising a target-hybridizing sequence substantially corresponding to a nucleotide sequence selected from SEQ ID NOs: 84, 5, and 12;

(d) a fourth target region corresponding to nucleotide positions 6057 to 7101 of SEQ ID NO:156, wherein if the fourth target region is amplified, then the at least two amplification oligomers comprise (i) at least one oligomer comprising a target-hybridizing sequence substantially corresponding to a nucleotide sequence selected from SEQ ID NOs: 95, 85, and 96; and (ii) at least one oligomer comprising a target-hybridizing sequence substantially corresponding to a nucleotide sequence selected from SEQ ID NOs: 1, 11, and 18;

(e) a fifth target region corresponding to nucleotide positions 5077 to 6290 of SEQ ID NO:156, wherein if the fifth target region is amplified, then the at least two amplification oligomers comprise (i) at least one oligomer comprising a target-hybridizing sequence substantially corresponding to a nucleotide sequence selected from SEQ ID NOs: 97, 98, and 99; and (ii) at least one oligomer comprising a target-hybridizing sequence substantially corresponding to a nucleotide sequence selected from SEQ ID NOs: 19, 3, and 7;

(f) a sixth target region corresponding to nucleotide positions 4240 to 5280 of SEQ ID NO:156, wherein if the sixth target region is amplified, then the at least two amplification oligomers comprise (i) at least one oligomer comprising a target-hybridizing sequence substantially corresponding to a nucleotide sequence selected from SEQ ID NOs: 23, 8, and 26; and (ii) at least one oligomer comprising a target-hybridizing sequence substantially corresponding to a nucleotide sequence selected from SEQ ID NOs: 100, 10, and 9; and (g) a seventh target region corresponding to nucleotide positions 3296 to 4466 of SEQ ID NO:156, wherein if the seventh target region is amplified, then the at least two amplification oligomers comprise (i) at least one oligomer comprising a target-hybridizing sequence substantially corresponding to a nucleotide sequence selected from SEQ ID NOs: 101, 15, and 6; and (ii) at least one oligomer comprising a target-hybridizing sequence substantially corresponding to a nucleotide sequence selected from SEQ ID NOs: 17, 74, and 27.

In more particular embodiments of the method for determining HCV-1b genotype information as above, the at least one amplification oligomer of one or more of (a)(i), (a)(ii), (b)(i), (b)(ii), (c)(i), (c)(ii), (d)(i), (d)(ii), (e)(i), (e)(ii), (f)(i), (f)(ii), (g)(i), and (g)(ii) comprises or consists of the specified nucleotide sequence.

In certain variations of the method for determining HCV-1 b genotype information, each of the first through seventh target regions of (a) through (g) are amplified to produce at least one amplification product corresponding to each of the HCV-1b target regions, and the detecting step comprises detecting the nucleobase at one or more positions within each of the seven amplification products. In some such variations, the contacting step includes contacting the sample with each of the oligomers of (a)(i); each of the oligomers of (a)(ii); each of the oligomers of (b)(i); each of the oligomers of (b)(ii); each of the oligomers of (c)(i); each of the oligomers of (c)(ii); each of the oligomers of (d)(i); each of the oligomers of (d)(ii); each of the oligomers of (e)(i); each of the oligomers of (e)(ii); each of the oligomers of (f)(i); each of the oligomers of (f)(ii); each of the oligomers of (g)(i); and each of the oligomers of (g)(ii).

In some embodiments of a method for determining at least partial genotype information for HCV-1a or HCV-1b, the detecting step includes sequencing the at least one amplification product. Suitable sequencing techniques include single molecule real time (SMRT) sequencing, chain terminator sequencing (Sanger sequencing), nanopore sequencing, massively parallel sequencing, pyrosequencing, polony sequencing, sequencing by ligation, ion semiconductor sequencing and DNA nanoball sequencing.

In other variations, the detecting step includes detecting, in a hybridization assay, an ability of the at least one amplification product to hybridize to a SNP-specific probe oligomer, such as, e.g., a SNP-specific probe oligomer comprising a detectable label. In yet other variations, the detecting step includes detecting, in an amplification-based assay, an ability of a SNP-specific amplification oligomer to amplify a region of the at least one amplification product.

In another aspect, the present invention provides a combination of at least two oligomers for amplifying at least one target region of a hepatitis C virus type 1a (HCV-1a) target nucleic acid present in a sample. The oligomer combination includes at least two amplification oligomers for amplifying the at least one target region and, optionally, at least one capture probe oligomer comprising a nucleotide sequence that hybridizes to the HCV-1a target nucleic acid, wherein the at least one capture probe further comprises a nucleotide sequence or moiety that binds to an immobilized probe. In some embodiments, the at least one target region and corresponding amplification oligomers are selected from the following:

(a) a first target region corresponding to nucleotide positions 8522 to 9372 of SEQ ID NO:155, wherein if the first target region is amplified, then the at least two amplification oligomers comprise (i) at least one oligomer comprising a target-hybridizing sequence substantially corresponding to a nucleotide sequence selected from SEQ ID NOs: 65, 43, and 34; and (ii) at least one oligomer comprising a target-hybridizing sequence substantially corresponding to a nucleotide sequence selected from SEQ ID NOs: 69, 38, and 41;

(b) a second target region corresponding to nucleotide positions 7788 to 8838 of SEQ ID NO:155, wherein if the second target region is amplified, then the at least two amplification oligomers comprise (i) at least one oligomer comprising a target-hybridizing sequence substantially corresponding to a nucleotide sequence selected from SEQ ID NOs: 57, 63, and 28; and (ii) at least one oligomer comprising a target-hybridizing sequence substantially corresponding to a nucleotide sequence selected from SEQ ID NOs: 40, 35, and 42;

(c) a third target region corresponding to nucleotide positions 6966 to 7970 of SEQ ID NO:155, wherein if the third target region is amplified, then the at least two amplification oligomers comprise (i) at least one oligomer comprising a target-hybridizing sequence substantially corresponding to a nucleotide sequence selected from SEQ ID NOs: 60, 58, and 36; and (ii) at least one oligomer comprising a target-hybridizing sequence substantially corresponding to a nucleotide sequence selected from SEQ ID NOs: 31, 73, and 62;

(d) a fourth target region corresponding to nucleotide positions 6076 to 7117 of SEQ ID NO:155, wherein if the fourth target region is amplified, then the at least two amplification oligomers comprise (i) at least one oligomer comprising a target-hybridizing sequence substantially corresponding to a nucleotide sequence selected from SEQ ID NOs: 55, 70, and 29; and (ii) at least one oligomer comprising a target-hybridizing sequence substantially corresponding to a nucleotide sequence selected from SEQ ID NOs: 46, 45, and 61;

(e) a fifth target region corresponding to nucleotide positions 5094 to 6304 of SEQ ID NO:155, wherein if the fifth target region is amplified, then the at least two amplification oligomers comprise (i) at least one oligomer comprising a target-hybridizing sequence substantially corresponding to a nucleotide sequence selected from SEQ ID NOs: 39, 44, and 68; and (ii) at least one oligomer comprising a target-hybridizing sequence substantially corresponding to a nucleotide sequence selected from SEQ ID NOs: 47, 51, and 59;

(f) a sixth target region corresponding to nucleotide positions 4258 to 5297 of SEQ ID NO:155, wherein if the sixth target region is amplified, then the at least two amplification oligomers comprise (i) at least one oligomer comprising a target-hybridizing sequence substantially corresponding to a nucleotide sequence selected from SEQ ID NOs: 52, 49, and 72; and (ii) at least one oligomer comprising a target-hybridizing sequence substantially corresponding to a nucleotide sequence selected from SEQ ID NOs: 37, 75, and 53; and (g) a seventh target region corresponding to nucleotide positions 3434 to 4482 of SEQ ID NO:155, wherein if the seventh target region is amplified, then the at least two amplification oligomers comprise (i) at least one oligomer comprising a target-hybridizing sequence substantially corresponding to a nucleotide sequence selected from SEQ ID NOs: 77, 79, and 81; and (ii) at least one oligomer comprising a target-hybridizing sequence substantially corresponding to a nucleotide sequence selected from SEQ ID NOs: 78, 80, and 71.

In more particular embodiments of the oligomer combination for amplifying at least one target region of a HCV-1a, the at least one amplification oligomer of one or more of (a)(i), (a)(ii), (b)(i), (b)(ii), (c)(i), (c)(ii), (d)(i), (d)(ii), (e)(i), (e)(ii), (f)(i), (f)(ii), (g)(i), and (g)(ii) comprises or consists of the specified nucleotide sequence.

In some variations, the oligomer combination includes amplification oligomers for amplifying more than one HCV-1a target region. In some such variations, the oligomer combination comprises the at least one oligomer of (a)(i); the at least one oligomer of (a)(ii); the at least one oligomer of (b)(i); the at least one oligomer of (b)(ii); the at least one oligomer of (c)(i); the at least one oligomer of (c)(ii); the at least one oligomer of (d)(i); the at least one oligomer of (d)(ii); the at least one oligomer of (e)(i); the at least one oligomer of (e)(ii); the at least one oligomer of (f)(i); the at least one oligomer of (f)(ii); the at least one oligomer of (g)(i); and the at least one oligomer of (g)(ii). In other such variations, the oligomer combination comprises each of the oligomers of (a)(i); each of the oligomers of (a)(ii); each of the oligomers of (b)(i); each of the oligomers of (b)(ii); each of the oligomers of (c)(i); each of the oligomers of (c)(ii); each of the oligomers of (d)(i); each of the oligomers of (d)(ii); each of the oligomers of (e)(i); each of the oligomers of (e)(ii); each of the oligomers of (f)(i); each of the oligomers of (f)(ii); each of the oligomers of (g)(i); and each of the oligomers of (g)(ii).

In yet another aspect, the present invention provides a combination of at least two oligomers for amplifying at least one target region of a hepatitis C virus type 1b (HCV-1b) target nucleic acid present in a sample. The oligomer combination includes at least two amplification oligomers for amplifying the at least one target region and, optionally, at least one capture probe oligomer comprising a nucleotide sequence that hybridizes to the HCV-1b target nucleic acid, wherein the at least one capture probe further comprises a nucleotide sequence or moiety that binds to an immobilized probe. In some embodiments, the at least one target region and corresponding amplification oligomers are selected from the following:

(a) a first target region corresponding to nucleotide positions 8504 to 9350 of SEQ ID NO:156, wherein if the first target region is amplified, then the at least two amplification oligomers comprise (i) at least one oligomer comprising a target-hybridizing sequence substantially corresponding to a nucleotide sequence selected from SEQ ID NOs: 21, 86, and 88; and (ii) at least one oligomer comprising a target-hybridizing sequence substantially corresponding to a nucleotide sequence selected from SEQ ID NOs: 76, 87, and 89;

(b) a second target region corresponding to nucleotide positions 7771 to 8618 of SEQ ID NO:156, wherein if the second target region is amplified, then the at least two amplification oligomers comprise (i) at least one oligomer comprising a target-hybridizing sequence substantially corresponding to a nucleotide sequence selected from SEQ ID NOs: 82, 4, and 2; and (ii) at least one oligomer comprising a target-hybridizing sequence substantially corresponding to a nucleotide sequence selected from SEQ ID NOs: 90, 92, and 91;

(c) a third target region corresponding to nucleotide positions 6956 to 7966 of SEQ ID NO:156, wherein if the third target region is amplified, then the at least two amplification oligomers comprise (i) at least one oligomer comprising a target-hybridizing sequence substantially corresponding to a nucleotide sequence selected from SEQ ID NOs: 83, 24, and 94; and (ii) at least one oligomer comprising a target-hybridizing sequence substantially corresponding to a nucleotide sequence selected from SEQ ID NOs: 84, 5, and 12;

(d) a fourth target region corresponding to nucleotide positions 6057 to 7101 of SEQ ID NO:156, wherein if the fourth target region is amplified, then the at least two amplification oligomers comprise (i) at least one oligomer comprising a target-hybridizing sequence substantially corresponding to a nucleotide sequence selected from SEQ ID NOs: 95, 85, and 96; and (ii) at least one oligomer comprising a target-hybridizing sequence substantially corresponding to a nucleotide sequence selected from SEQ ID NOs: 1, 11, and 18;

(e) a fifth target region corresponding to nucleotide positions 5077 to 6290 of SEQ ID NO:156, wherein if the fifth target region is amplified, then the at least two amplification oligomers comprise (i) at least one oligomer comprising a target-hybridizing sequence substantially corresponding to a nucleotide sequence selected from SEQ ID NOs: 97, 98, and 99; and (ii) at least one oligomer comprising a target-hybridizing sequence substantially corresponding to a nucleotide sequence selected from SEQ ID NOs: 19, 3, and 7;

(f) a sixth target region corresponding to nucleotide positions 4240 to 5280 of SEQ ID NO:156, wherein if the sixth target region is amplified, then the at least two amplification oligomers comprise (i) at least one oligomer comprising a target-hybridizing sequence substantially corresponding to a nucleotide sequence selected from SEQ ID NOs: 23, 8, and 26; and (ii) at least one oligomer comprising a target-hybridizing sequence substantially corresponding to a nucleotide sequence selected from SEQ ID NOs: 100, 10, and 9; and (g) a seventh target region corresponding to nucleotide positions 3296 to 4466 of SEQ ID NO: 156, wherein if the seventh target region is amplified, then the at least two amplification oligomers comprise (i) at least one oligomer comprising a target-hybridizing sequence substantially corresponding to a nucleotide sequence selected from SEQ ID NOs: 101, 15, and 6; and (ii) at least one oligomer comprising a target-hybridizing sequence substantially corresponding to a nucleotide sequence selected from SEQ ID NOs: 17, 74, and 27.

In more particular embodiments of the oligomer combination for amplifying at least one target region of a HCV-1b, the at least one amplification oligomer of one or more of (a)(i), (a)(ii), (b)(i), (b)(ii), (c)(i), (c)(ii), (d)(i), (d)(ii), (e)(i), (e)(ii), (f)(i), (f)(ii), (g)(i), and (g)(ii) comprises or consists of the specified nucleotide sequence.

In some variations, the oligomer combination includes amplification oligomers for amplifying more than one HCV-1b target region. In some such variations, the oligomer combination comprises the at least one oligomer of (a)(i); the at least one oligomer of (a)(ii); the at least one oligomer of (b)(i); the at least one oligomer of (b)(ii); the at least one oligomer of (c)(i); the at least one oligomer of (c)(ii); the at least one oligomer of (d)(i); the at least one oligomer of (d)(ii); the at least one oligomer of (e)(i); the at least one oligomer of (e)(ii); the at least one oligomer of (f)(i); the at least one oligomer of (f)(ii); the at least one oligomer of (g)(i); and the at least one oligomer of (g)(ii). In other such variations, the oligomer combination comprises each of the oligomers of (a)(i); each of the oligomers of (a)(ii); each of the oligomers of (b)(i); each of the oligomers of (b)(ii); each of the oligomers of (c)(i); each of the oligomers of (c)(ii); each of the oligomers of (d)(i); each of the oligomers of (d)(ii); each of the oligomers of (e)(i); each of the oligomers of (e)(ii); each of the oligomers of (f)(i); each of the oligomers of (f)(ii); each of the oligomers of (g)(i); and each of the oligomers of (g)(ii).

These and other aspects of the invention will become evident upon reference to the following detailed description of the invention and the attached drawings.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain hepatitis C virus type 1a (HCV-1a) and/or type 1b (HCV-1b) or components thereof, such as nucleic acids or fragments of nucleic acids. Samples include "biological samples" which include any tissue or material derived from a living or dead human that may contain HCV-1a and/or HCV-1b or target nucleic acid derived therefrom, including, e.g., peripheral blood, plasma, serum, lymph node, gastrointestinal tissue (e.g., liver), or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar, and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide" unit as used herein (e.g., a non-nucleotide linker) is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified.

By "isolated" it is meant that a biological constituent (e.g., a sample containing a target nucleic acid) is taken from its natural milieu, but the term does not connote any degree of purification.

The term "target region" as used herein refers to the particular region of the target nucleic acid that is to be amplified. The "target region" includes the complexing sequences to which oligonucleotides (e.g., priming oligonucleotides and/or promoter oligonucleotides) complex during an amplification processes (e.g., PCR, TMA). Where the target nucleic acid is originally single-stranded, the term "target region" will also refer to the sequence complementary to the "target region" as present in the target nucleic acid. Where the target nucleic acid is originally double-stranded, the term "target sequence" refers to both the sense (+) and antisense (−) strands.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various subtypes of HCV 1a or 1b. It is understood that other reasons exist for configuring a target-hybridizing sequence to have less than 100% complementarity to a target nucleic acid.

Oligomer target-hybridizing sequences defined herein by reference to a specific sequence (e.g., by reference to a sequence substantially corresponding to or substantially complementary to a region within SEQ ID NO: 155 or 156) are also understood to include functional complements thereof, unless the context clearly dictates otherwise. Thus, for example, where target-hybridizing regions of first and second amplification oligomers are defined by reference to specific sequences corresponding, respectively, to sense and antisense strands of a target nucleic acid, it is understood that the amplification oligomer combination may include a functional combination of first and second amplification oligomers having target-hybridizing sequences that are the respective complements of the specific reference sequences.

The term "targets a sequence" as used herein in reference to a region of HCV-1a or HCV-1b nucleic acid refers to a process whereby an oligonucleotide hybridizes to the target sequence in a manner that allows for amplification of HCV target nucleic acid and/or detection of at least partial genotype information as described herein. In one preferred embodiment, the oligonucleotide is complementary with the targeted HCV nucleic acid sequence and contains no mismatches. In another preferred embodiment, the oligonucleotide is complementary but contains 1, 2, 3, 4, or 5 mismatches with the targeted HCV nucleic acid sequence. Preferably, the oligonucleotide that hybridizes to the HCV nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an amplification oligonucleotide, detection probe, or other oligonucleotide is designed to have a polynucleotide sequence that could target a sequence of the referenced HCV-1a or HCV-1b target region. Such an oligonucleotide is not limited to targeting that sequence only, but is rather useful as a composition, in a kit, or in a method for targeting an HCV target nucleic acid. The oligonucleotide is designed to function as a component of an assay for amplification and detection of HCV from a sample, and therefore is designed to target HCV in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that amplification and/or accurate detection of target nucleic acid in a sample, including accurate detection of at least partial genotype information as described herein, can be determined. The term "configured to" denotes an actual arrangement of the polynucleotide sequence configuration of the amplification oligonucleotide target-hybridizing sequence.

The term "fragment," as used herein in reference to the HCV-1a or HCV-1 b targeted nucleic acid, refers to a piece of contiguous nucleic acid. In certain embodiments, the fragment includes contiguous nucleotides from an HCV-1a or HCV-1b RNA, wherein the number of contiguous nucleotides in the fragment are less than that for the entire HCV RNA.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a HCV-1a or HCV-1b nucleic acid, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

In the context of HCV nucleic acid sequences, "correspondence" to another sequence (e.g., regions, fragments, nucleotide positions, or the like) is based on the convention of numbering according to nucleotide position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to a "target region corresponding to nucleotide positions [X] to [Y]" of a specified HCV nucleotide sequence represents referral to a collection of equivalent positions in other recognized HCV nucleic acids. In addition, reference herein to "amplifying" a "target region corresponding to nucleotide positions [X] to [Y]" of a specified HCV nucleotide sequence includes reference to an amplified target region falling within about 50 to about 100 nucleotides of either of the specified [X] and/or [Y] endpoints.

As used herein, the term "single nucleotide polymorphism" or "SNP," refers to any position along a nucleotide sequence that has one or more variant nucleotides. In the context of HCV nucleic acids and methods of genotyping as described herein, a "SNP" is generally defined as a difference from a baseline reference nucleotide sequence or as a difference found between a subset of HCV nucleic acids of particular type (e.g., type 1) or subtype (e.g., 1a or 1b).

The interchangeable terms "oligomer," "oligo," and "oligonucleotide" refer to a polynucleotide having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. It is understood that when referring to ranges for percentages between substantially corresponding nucleic acids, that the range is inclusive of all whole and partial numbers (e.g., 98%, 97.64%, etc.). Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider." Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. It is understood that ranges for percent complementarity are inclusive of all whole and partial numbers (e.g., at least 90% includes 90, 94, 96.114 and etc.). An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), reverse transcription polymerase chain reaction (RT-PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422, 252; 5,547,861; and 5,648,211; each incorporated by reference herein).

"Polymerase chain reaction" (PCR) uses a DNA polymerase, pairs of primers, and thermal cycling to synthesize multiple copies of two complementary strands of dsDNA or from a cDNA (see, e.g., U.S. Pat. Nos. 4,683,195; 4,683, 202; and 4,800,159; each incorporated by reference herein). Generally, this process for amplifying a target region includes introducing an excess of at least two oligonucleotide primers (forward and reverse) to a mixture containing the desired target nucleic acid, followed by a precise sequence of thermal cycling in the presence of a DNA polymerase. To effect amplification, the mixture is denatured and the primers then annealed to their respective target sequences within complementary strands of the target nucleic acid. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The amplified segments created by the PCR process itself are, themselves, efficient templates for subsequent PCR amplifications. "Reverse transcription polymerase chain reaction" (RT-PCR) is a variant of PCR in which an RNA strand is reverse transcribed into its DNA complement (cDNA) using a reverse transcriptase, and the resulting cDNA is amplified using PCR.

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. Variations of transcription-associated amplification are well-known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein).

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Some amplicons generated according to this disclosure will comprise 5' and 3' ends that are at least 80% (inclusive of all whole and partial numbers from 80-100%) identical to an amplification oligomer presented in the Sequence Listing or a complement thereof. Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons, all within the spirit and scope of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see. e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Habor, N Y, 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-OU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues, that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning. A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Appropriate hybridization conditions are well-known in the art, may be predicted based on sequence composition, or can be determined by using routine testing methods (see, e.g., Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent amplification and/or detection of HCV nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

BRIEF DESCRIPTION OF THE DRAWINGS

FIGS. 1A-1E illustrate a reference sequence for hepatitis C virus subtype 1a polyprotein gene, complete eds (SEQ ID NO: 155), found at GenBank under accession number AF009606.1 and GI:2316097.

FIGS. 2A-2E illustrate a reference sequence for hepatitis C virus complete genome sequence (SEQ ID NO: 156), found at GenBank under accession number AJ000009.1 and GI:2764397.

DETAILED DESCRIPTION OF THE INVENTION

The present invention provides compositions, kits, and methods for amplifying one or more selected regions of an HCV type 1 nucleic acid from a sample, particularly HCV type 1a (HCV-1a) or type 1b (HCV-1b). The amplicon(s) produced by the amplification method may be used, for example, for subsequent characterization of the HCV nucleic acid, such as obtaining at least partial genotype information by detecting the nucleobase at one or more nucleotide positions in the amplicon. The compositions, kits, and methods disclosed herein are useful, e.g., for determining the subtype of an HCV type 1 nucleic acid as either subtype 1a or subtype 1b and/or detecting the presence of particular nucleotide variations in an HCV-1a or -1b nucleic acid. Such determinations may in turn be useful for, e.g., stratifying and interpreting efficacy and resistance data during clinical testing of an HCV drug or for tailoring treatment schedules with one or more HCV drugs according to the particular HCV genotype.

Accordingly, in one aspect, the present invention provides a method for determining at least partial genotype information for hepatitis C virus type 1a (HCV-1a) or type 1b (HCV-1b) in a sample, wherein the method generally includes the following steps: (1) contacting a sample, which is suspected of containing HCV-1a or HCV-1b, with at least two amplification oligomers for amplifying at least one target region of an HCV-1a or HCV-1 b target nucleic acid; (2) performing at least one in vitro nucleic acid amplification reaction, wherein any HCV-1a or HCV-1b target nucleic acid present in the sample is used as a template for generating at least one amplification product corresponding to the at least one target region; and (3) detecting the nucleobase at one or more nucleotide positions within the at least one amplification product, thereby determining at least partial genotype information for the HCV-1a or HCV-1b in the sample.

In particular embodiments of the present invention, the at least two amplification oligomers are (i) at least one amplification oligomer comprising an HCV-1a or -1b target-hybridizing region substantially corresponding to at least one sense oligomer sequence depicted in Table 1 (see Example 2, infra), and (ii) at least one amplification oligomer comprising an HCV-1a or -1b target hybridizing region substantially corresponding to at least one antisense oligomer sequence depicted in Table 1, where the target-hybridizing sequences are selected such that, for any oligomer pair, the antisense sequence is situated downstream of the sense sequence (i.e., the at least two amplification oligomers are situated such that they flank a target region to be amplified). In particular variations, the sense and/or antisense target-hybridizing sequence comprises or consists of the sense and/or antisense sequence selected from Table 1.

In more specific variations of a method for determining HCV-1a genotype information, the one or more target regions and corresponding amplification oligomers are selected from the following:

(a) a first target region corresponding to nucleotide positions 8522 to 9372 of SEQ ID NO:155, where if the first target region is amplified, then the at least two amplification oligomers include (i) at least one oligomer comprising a target-hybridizing sequence substantially corresponding to a nucleotide sequence selected from SEQ ID NOs: 65, 43, and 34; and (ii) at least one oligomer comprising a target-hybridizing sequence substantially corresponding to a nucleotide sequence selected from SEQ ID NOs: 69, 38, and 41;

(b) a second target region corresponding to nucleotide positions 7788 to 8838 of SEQ ID NO:155, where if the second target region is amplified, then the at least two amplification oligomers include (i) at least one oligomer comprising a target-hybridizing sequence substantially corresponding to a nucleotide sequence selected from SEQ ID NOs: 57, 63, and 28; and (ii) at least one oligomer comprising a target-hybridizing sequence substantially corresponding to a nucleotide sequence selected from SEQ ID NOs: 40, 35, and 42;

(c) a third target region corresponding to nucleotide positions 6966 to 7970 of SEQ ID NO:155, where if the third target region is amplified, then the at least two amplification oligomers include (i) at least one oligomer comprising a target-hybridizing sequence substantially corresponding to a nucleotide sequence selected from SEQ ID NOs: 60, 58, and 36; and (ii) at least one oligomer comprising a target-hybridizing sequence substantially corresponding to a nucleotide sequence selected from SEQ ID NOs: 31, 73, and 62;

(d) a fourth target region corresponding to nucleotide positions 6076 to 7117 of SEQ ID NO:155, where if the fourth target region is amplified, then the at least two amplification oligomers include (i) at least one oligomer comprising a target-hybridizing sequence substantially corresponding to a nucleotide sequence selected from SEQ ID NOs: 55, 70, and 29; and (ii) at least one oligomer comprising a target-hybridizing sequence substantially corresponding to a nucleotide sequence selected from SEQ ID NOs: 46, 45, and 61;

(e) a fifth target region corresponding to nucleotide positions 5094 to 6304 of SEQ ID NO:155, where if the fifth target region is amplified, then the at least two amplification oligomers include (i) at least one oligomer comprising a target-hybridizing sequence substantially corresponding to a nucleotide sequence selected from SEQ ID NOs: 39, 44, and 68; and (ii) at least one oligomer comprising a target-hybridizing sequence substantially corresponding to a nucleotide sequence selected from SEQ ID NOs: 47, 51, and 59;

(f) a sixth target region corresponding to nucleotide positions 4258 to 5297 of SEQ ID NO:155, where if the sixth target region is amplified, then the at least two amplification oligomers include (i) at least one oligomer comprising a target-hybridizing sequence substantially corresponding to a nucleotide sequence selected from SEQ ID NOs: 52, 49, and 72; and (ii) at least one oligomer comprising a target-hybridizing sequence substantially corresponding to a nucleotide sequence selected from SEQ ID NOs: 37, 75, and 53; and (g) a seventh target region corresponding to nucleotide positions 3434 to 4482 of SEQ ID NO:155, where if the seventh target region is amplified, then the at least two amplification oligomers include (i) at least one oligomer comprising a target-hybridizing sequence substantially corresponding to a nucleotide sequence selected from SEQ ID NOs: 77, 79, and 81; and (ii) at least one oligomer comprising a target-hybridizing sequence substantially corresponding to a nucleotide sequence selected from SEQ ID NOs: 78, 80, and 71.

In certain embodiments of the method for determining HCV-1a genotype information, one, two, three, four, five, six, or seven of the target regions of (a) through (g) are amplified. In preferred variations, each of the first through seventh target regions of (a) through (g) are amplified to produce at least one amplification product corresponding to each of the HCV-1a target regions. In such variations, the detecting step typically includes detecting the nucleobase at one or more positions within each of the seven amplification products. Further, the method can include the use of more than one sense/antisense oligomer pair for any one or more target region to be amplified. In some such embodiments, the contacting step includes contacting the sample with each of the oligomers of (a)(i) through (g)(ii) as specified above for HCV-1a.

In more specific variations of a method for determining HCV-1b genotype information, the one or more target regions and corresponding amplification oligomers are selected from the following:

(a) a first target region corresponding to nucleotide positions 8504 to 9350 of SEQ ID NO:156, where if the first target region is amplified, then the at least two amplification oligomers include (i) at least one oligomer comprising a target-hybridizing sequence substantially corresponding to a nucleotide sequence selected from SEQ ID NOs: 21, 86, and 88; and (ii) at least one oligomer comprising a target-hybridizing sequence substantially corresponding to a nucleotide sequence selected from SEQ ID NOs: 76, 87, and 89;

(b) a second target region corresponding to nucleotide positions 7771 to 8618 of SEQ ID NO:156, where if the second target region is amplified, then the at least two amplification oligomers include (i) at least one oligomer comprising a target-hybridizing sequence substantially corresponding to a nucleotide sequence selected from SEQ ID NOs: 82, 4, and 2; and (ii) at least one oligomer comprising a target-hybridizing sequence substantially corresponding to a nucleotide sequence selected from SEQ ID NOs: 90, 92, and 91;

(c) a third target region corresponding to nucleotide positions 6956 to 7966 of SEQ ID NO:156, where if the third target region is amplified, then the at least two amplification oligomers include (i) at least one oligomer comprising a target-hybridizing sequence substantially corresponding to a nucleotide sequence selected from SEQ ID NOs: 83, 24, and 94; and (ii) at least one oligomer comprising a target-hybridizing sequence substantially corresponding to a nucleotide sequence selected from SEQ ID NOs: 84, 5, and 12;

(d) a fourth target region corresponding to nucleotide positions 6057 to 7101 of SEQ ID NO:156, where if the fourth target region is amplified, then the at least two amplification oligomers include (i) at least one oligomer comprising a target-hybridizing sequence substantially corresponding to a nucleotide sequence selected from SEQ ID NOs: 95, 85, and 96; and (ii) at least one oligomer comprising a target-hybridizing sequence substantially corresponding to a nucleotide sequence selected from SEQ ID NOs: 1, 11, and 18;

(e) a fifth target region corresponding to nucleotide positions 5077 to 6290 of SEQ ID NO:156, where if the fifth target region is amplified, then the at least two amplification oligomers include (i) at least one oligomer comprising a target-hybridizing sequence substantially corresponding to a nucleotide sequence selected from SEQ ID NOs: 97, 98, and 99; and (ii) at least one oligomer comprising a target-hybridizing sequence substantially corresponding to a nucleotide sequence selected from SEQ ID NOs: 19, 3, and 7;

(f) a sixth target region corresponding to nucleotide positions 4240 to 5280 of SEQ ID NO:156, where if the sixth target region is amplified, then the at least two amplification oligomers include (i) at least one oligomer comprising a target-hybridizing sequence substantially corresponding to a nucleotide sequence selected from SEQ ID NOs: 23, 8, and 26; and (ii) at least one oligomer comprising a target-hybridizing sequence substantially corresponding to a nucleotide sequence selected from SEQ ID NOs: 100, 10, and 9; and (g) a seventh target region corresponding to nucleotide positions 3296 to 4466 of SEQ ID NO:156, where if the seventh target region is amplified, then the at least two amplification oligomers include (i) at least one oligomer comprising a target-hybridizing sequence substantially corresponding to a nucleotide sequence selected from SEQ ID NOs: 101, 15, and 6; and (ii) at least one oligomer comprising a target-hybridizing sequence substantially corresponding to a nucleotide sequence selected from SEQ ID NOs: 17, 74, and 27.

In certain embodiments of the method for determining HCV-1b genotype information, one, two, three, four, five, six, or seven of the target regions of (a) through (g) are amplified. In preferred variations, each of the first through seventh target regions of (a) through (g) are amplified to produce at least one amplification product corresponding to each of the HCV-1b target regions. In such variations, the detecting step typically includes detecting the nucleobase at one or more positions within each of the seven amplification products. Further, the method can include the use of more than one sense/antisense oligomer pair for any one or more target region to be amplified. In some such embodiments, the contacting step includes contacting the sample with each of the oligomers of (a)(i) through (g)(ii) as specified above for HCV-1 b.

In certain embodiments, the method further includes purifying the HCV target nucleic acid from other components in the sample before the contacting step. Such purification may include methods of separating and/or concentrating HCV contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains HCV nucleic acid and other sample components.

In some embodiments, an HCV target nucleic is selectively separated from other sample components by hybridizing the HCV target nucleic acid to a capture probe oligomer. In some variations, the capture probe oligomer comprises a target-hybridizing sequence configured to specifically hybridize to an HCV nucleic acid target sequence so as to form a target-sequence:capture-probe complex that is separated from sample components. In other variations, the capture probe oligomer uses a target-hybridizing sequence that includes randomized or non-randomized poly-GU, poly-GT, or poly U sequences to bind non-specifically to an HCV target nucleic acid so as to form a target-sequence:capture-probe complex that is separated from sample components. In specific variations, the capture probe oligomer comprises a target-hybridizing sequence that includes a randomized poly-(k) sequence comprising G and T nucleotides or G and U nucleotides (e.g., a $(k)_{18}$ sequence), such as described, for example, in WIPO Publication No. 2008/016988, incorporated by reference herein.

In a preferred variation, the target capture binds the HCV target:capture-probe complex to an immobilized probe to form a target:capture-probe:immobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to the HCV target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$ or $T_{0-3}A_{10-40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle.

In particular variations, the capture probe oligomer comprising a randomized poly-(k) nucleotide sequence (e.g., $(k)_{18}$) and a 3' tail portion, preferably a substantially homopolymeric tail of about 10 to 40 nt (e.g., $T_{0-3}A_{10-40}$).

Target capture typically occurs in a solution phase mixture that contains one or more capture probe oligomers that hybridize to the HCV target nucleic acid under hybridizing conditions, usually at a temperature higher than the $T_m$ of the tail-sequence:immobilized-probe-sequence duplex. For embodiments comprising a capture probe tail, the HCV-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:HCV-target may be washed one or more times to further remove other sample components. Preferred embodiments use a particulate solid support, such as paramagnetic beads, so that particles with the attached HCV-target:capture-probe:immobilized-probe complex may be suspended in a washing solution and retrieved from the washing solution, preferably by using magnetic attraction. To limit the number of handling steps, the HCV target nucleic acid may be amplified by simply mixing the HCV target nucleic acid in the complex on the support with amplification oligomers and proceeding with amplification steps.

Amplifying an HCV target region utilizes an in vitro amplification reaction using at least two amplification oligomers that flank a target region to be amplified. As previously indicated, particularly suitable amplification oligomers for amplification of selected HCV-1a and HCV-1b target regions include a target-hybridizing region substantially corresponding to, comprising, or consisting of a nucleotide sequence as shown in Table 1, infra. Suitable amplification methods include, for example, replicase-mediated amplification; polymerase chain reaction (PCR), including reverse transcription polymerase chain reaction (RT-PCR); ligase chain reaction (LCR); strand-displacement amplification (SDA); and transcription-mediated or transcription-associated amplification (TMA). Such amplification methods are well-known in the art (see. e.g., paragraphs [44]-[46], supra) and are readily used in accordance with the methods of the present invention.

Once one or more HCV target regions are amplified to produce one or more corresponding amplification products, the amplification product(s) may be used in subsequent procedures for detecting the nucleobase at one or more nucleotide positions, thereby generating at least partial genotype information for the HCV target nucleic acid in the sample.

In some embodiments of a method for determining at least partial genotype information for HCV-1a target nucleic acid, the nucleobase at one or more nucleotide positions is detected for amplification product(s) representing a region of the HCV-1a target nucleic acid corresponding to positions 3434 to 9372 of SEQ ID NO: 155, or one or more subregions within this region. In certain embodiments, where one, two, three, four, five, six, or seven of the target regions of (a) through (g) as set forth above for HCV-1a above (see, e.g., paragraph [67]) are amplified, the nucleobase at one or more positions is detected for each amplicon produced. In some preferred variations, where each of the first through seventh target regions of (a) through (g) are amplified to produce at least one amplification product corresponding to each of these HCV-1a target regions, the detecting step includes detecting the nucleobase at one or more positions within each of the HCV-1a seven amplification products.

In some embodiments of a method for determining at least partial genotype information for HCV-1b target nucleic acid, the nucleobase at one or more nucleotide positions is detected for amplification product(s) representing a region of the HCV-1b target nucleic acid corresponding to positions 3296 to 9350 of SEQ ID NO: 156, or one or more subregions within this region. In certain embodiments, where one, two, three, four, five, six, or seven of the target regions of (a) through (g) as set forth above for HCV-1b above (see, e.g., paragraph [69]) are amplified, the nucleobase at one or more positions is detected for each amplicon produced. In some preferred variations, where each of the first through seventh target regions of (a) through (g) are amplified to produce at least one amplification product corresponding to each of these HCV-1b target regions, the detecting step includes detecting the nucleobase at one or more positions within each of the seven HCV-1b amplification products.

In certain variations, detecting the nucleobase at one or more nucleotide positions includes sequencing the amplification product(s) corresponding to the one or more amplified target regions. Various suitable sequencing techniques are known in the art and are readily used for sequencing an HCV-1a or HCV-1b amplification product in accordance with the methods of the present invention. For example, in some embodiments, the sequencing of an amplification product comprises single molecule real time (SMRT) sequencing (see, e.g., Eid et al., Science 323:133-138, 2008; U.S. Pat. No. 8,153,375, each incorporated by reference herein). Reagents and instruments for performing SMRT sequencing are commercially available from Pacific Biosciences (Menlo Park, Calif.). In other embodiments, the sequencing of an amplification product comprises conventional chain terminator sequencing (also known as the Sanger sequencing method), which may be performed manually (e.g., using radioactive marker nucleotides) or in an automated format (e.g., using differentially dye-labeled nucleotides). In still other embodiments, the sequencing of an amplification product comprises. The method of claim 4, wherein said sequencing comprises nanopore sequencing, massively parallel sequencing, pyrosequencing, polony sequencing, sequencing by ligation, ion semiconductor sequencing and DNA nanoball sequencing (See e.g., Brenner et al., Nature Biotechnology, (2000) 18 (6): 630-634: Mardis, Annual Review of Genomics and Human Genetics (2008) 9: 387-402; Margulies, et al., Nature 437 (September 2005) 7057: 376-80; Rusk, Nat Meth (2011) 8(1): 44-44; Drmanac, R. et. al., Science, (2010) 327 (5961): 78-81; Porreca, Nature Biotechnology, (2010) 28:43-44; Clarke et al., (2009) Nature Nanotechnology 4 (4): 265-270).

In other embodiments, genotyping is performed using a technique other than direct sequencing of an amplification product to detecting one or more single nucleotide polymorphisms (SNPs). Various non-sequencing-based techniques for detecting genetic variations are known in the art and are readily used for detecting a SNP within an HCV-1a or HCV-1b amplification product in accordance with the methods of the present invention.

For example, in some embodiments, a variant sequence (i.e., a sequence containing one or more SNPs relative to a reference sequence) is detected using an amplification-based assay (e.g., PCR or TMA). In certain variations, the assay comprises the use of amplification oligomers that hybridize only to a variant or reference sequence (e.g., to the region of polymorphism or mutation). Both sets of amplification oligomers are used to amplify an HCV-1a or HCV-1b amplification product ("HCV-1a or HCV-1b amplification product template"). If only the amplification oligomers specific for the variant sequence ("SNP-specific amplification oligomers") result in an amplification product, then the nucleobase(s) associated with the one or more SNPs are detected within the corresponding positions of the HCV-1a or HCV-1b amplification product template. If only the amplification oligomers specific for the reference sequence result in an amplification product, then the HCV-1a or HCV-1b amplification product template has the reference sequence at the corresponding nucleotide positions.

In other embodiments utilizing a non-sequencing-based technique, variant sequences are detected using a hybridization assay. In a hybridization assay, the presence of absence of a given SNP or mutation is determined based on the ability of an HCV-1a or HCV-1b amplification product to hybridize to a probe oligomer specific for only a variant or reference sequence. Hybridization of a probe oligomer specific for the variant sequence ("SNP-specific probe oligomer" or "SNP-specific detection probe oligomer") indicates the presence of the nucleobase(s) associated with the one or more SNPs within the corresponding positions of the HCV-1a or HCV-1b amplification product. A variety of hybridization assays using a variety of technologies for hybridization and detection are known in the art and may be readily used for detection of variant sequences in accordance with the present invention.

Preferred embodiments of SNP-specific detection probe oligomers may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified HCV-1a or HCV-1b sequences may be unlabeled and detected indirectly (e.g., by binding of another binding partner to a moiety on the probe) or may be labeled with a variety of detectable labels. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. Nos. 5,118,801 and 5,312,728, supra). Methods for using such hairpin probes are well known in the art.

In yet other embodiments, a detection probe is a linear oligomer that does not substantially form conformations held by intramolecular bonds. In specific variations, a linear detection probe oligomer includes a chemiluminescent compound as the label, preferably an acridinium ester (AE) compound.

In other embodiments of the present invention, variant sequences are detected using a DNA chip hybridization assay. In this assay, a series of SNP-specific probe oligomers are affixed to a solid support. The DNA sample of interest is contacted with the DNA "chip" and hybridization to any one or more of the SNP-specific probe oligomers is detected. In some variations, the DNA chip assay is a GeneChip assay (Affymetrix, Santa Clara, Calif.; see e.g., U.S. Pat. Nos. 6,045,996; 5,925,525; and 5,858,659; each incorporated by reference herein). In other variations, a DNA microchip containing electronically captured probes (Nanogen, San Diego, Calif.) is utilized (see e.g., U.S. Pat. Nos. 6,017,696; 6,068,818; and 6,051,380; each incorporated by reference herein). In still further variations, an array technology based upon the segregation of fluids on a flat surface (chip) by differences in surface tension (ProtoGene, Palo Alto, Calif.) is utilized (see e.g., U.S. Pat. Nos. 6,001,311; 5,985,551; and 5,474,796; each incorporated by reference herein).

Additional detection assays that are suitable for use for detecting variant HCV sequences in accordance with the present invention include, for example, enzyme mismatch cleavage methods (e.g., Variagenics, U.S. Pat. Nos. 6,110,684; 5,958,692; 5,851,770; each incorporated by reference herein); polymerase chain reaction; branched hybridization methods (e.g., Chiron, U.S. Pat. Nos. 5,849,481; 5,710,264; 5,124,246; and 5,624,802; each incorporated by reference herein); rolling circle replication (e.g., U.S. Pat. Nos. 6,210,884 and 6,183,960, each incorporated by reference herein); NASBA (e.g., U.S. Pat. No. 5,409,818, each incorporated by reference herein); molecular beacon technology (e.g., U.S. Pat. No. 6,150,097, each incorporated by reference herein); E-sensor technology (Motorola, U.S. Pat. Nos. 6,248,229; 6,221,583; 6,013,170; and 6,063,573; each incorporated by reference herein); INVADER assay (Third Wave Technologies; see e.g., U.S. Pat. Nos. 5,846,717; 6,090,543; 6,001,567; 5,985,557; and 5,994,069; each incorporated by reference herein); cycling probe technology (e.g., U.S. Pat. Nos. 5,403,711; 5,011,769; and 5,660,988; each incorporated by reference herein); Dade Behring signal amplification methods (e.g., U.S. Pat. Nos. 6,121,001; 6,110,677; 5,914,230; 5,882,867; and 5,792,614; each incorporated by reference herein); ligase chain reaction (Bamay, *Proc. Natl. Acad. Sci. USA* 88:189-93, 1991; incorporated by reference herein); and sandwich hybridization methods (e.g., U.S. Pat. No. 5,288,609, incorporated by reference herein).

In another aspect, the present invention provides a combination of at least two oligomers for amplifying at least one target region of an HCV-1a or HCV-1b target nucleic acid present in a sample. The oligomer combination generally includes at least two amplification oligomers as described herein for amplifying one or more selected target regions of HCV-1a or HCV-1b target nucleic acid. In some embodiments, the oligomer combination further includes at least one capture probe oligomer comprising a nucleotide sequence that hybridizes to the HCV-1a or HCV-1b target nucleic acid, wherein the at least one capture probe further comprises a nucleotide sequence or moiety that binds to an immobilized probe.

Also provided by the subject invention is a reaction mixture for amplifying one or more selected target regions of an HCV-1a or HCV-1b target nucleic acid. A reaction mixture in accordance with the present invention at least comprises an oligomer combination as described herein for amplification of an HCV-1a or HCV-1b target nucleic acid. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., an RNA and/or DNA polymerase, such as, for example, a reverse transcriptase), and will typically include test sample components, in which a HCV target nucleic acid may or may not be present.

Also provided by the subject invention are kits for practicing the methods as described herein. A kit in accordance with the present invention at least comprises an oligomer combination as described herein for amplification of an HCV-1a or HCV-1b target nucleic acid. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., an RNA and/or DNA polymerase, such as, for example, a reverse transcriptase). Oligomers as described herein may be packaged in a variety of different embodiments, and those skilled in the art will appreciate that the invention embraces many different kit configurations. For example, a kit may include amplification oligomers for only one target region of an HCV-1a or HCV-1b target nucleic acid, or it may include amplification oligomers for multiple HCV-1a or HCV-1b target regions. In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Example 1

RT-PCR Amplification of Selected HCV Regions

This example describes the reverse transcription of a selected viral RNA region and subsequent PCR amplification of the generated 1st cDNA strand.

Materials

Reverse transcription of viral RNA was performed using the SuperScript® III First-Strand Synthesis System kit from Life Technologies (Carlsbad, Calif., Catalog Number 18080-051).

First-Strand cDNA was amplified using the Titanium® Taq PCR kit from Clontech (Mountain View, Calif., Catalog Number 639210).

Amplicons were purified using a MinElute PCR Purification Kit from Qiagen (Valencia, Calif., Catalog Number 28004).

Amplicons were quantitated on a Qubit® Fluorometer using Qubit® reagents from Life Technologies (Carlsbad, Calif., Catalog Numbers Q32866 and Q32851).

Amplicons were visualized on E-Gel® EX agarose gels from Life Technologies (Carlsbad, Calif., Catalog Number G 402002).

Viral RNA from clinical samples, in-vitro transcribed RNA from cloned clinical samples or cloned plasmid DNA, were used in the reverse-transcription amplification reactions.

Reverse transcription and PCR amplification reactions were run on either Rotor Gene Q instruments from Qiagen (Valencia, Calif., Catalog Number 901560) or Veriti® Thermal Cyclers from Life Technologies (Carlsbad, Calif., Catalog Numbers 4375786).

Methods

Reverse Transcription of Viral or Transcript RNA

First strand cDNA synthesis was performed using the SuperScript® IT First-Strand Synthesis System kit. The manufacturer's recommendations and protocol were followed with the exception of additional modifications as described below.

Eight µL of RNA was combined with 1 µL of random hexamer primers (50 ng/µL) and 1 µL of dNTPs (10 mM). The mixture was heated to 65° C. for five minutes in a thermal cycler and cooled down one ice for 1 minute. Ten µL of a prepared mastermix containing 2 µL of 10× Reverse Transcriptase buffer, 4 µL of magnesium chloride (25 mM), 2 µL of DTT (0.1 mM), 1 µL of RNAse OUT (40 u/µL) and 1 µL of SuperScript III enzyme was added to the cooled reaction mixture from above and mixed by up and down pipetting. The entire reaction mixture was incubated at 25° C. for 10 minutes, followed by 50° C. for 50 minutes, 85° C. for five minutes and then cooled on ice.

One µL of RNAse H enzyme (2 U/µL) was added and the reaction mix was incubated at 37° C. for 20 minutes followed by either short-term storage at 4° C. or long-term storage at −20° C.

PCR Amplification

A volume of 2.5 µL of the first cDNA strand reaction mix was combined with 47.5 µL of a mastermix consisting of 2.5 µL of PCR sense primer (10 µM), 2.5 µL of PCR anti-sense primer (10 µM), 5 µL of 10× Titanium Taq buffer, 1 µL of 50×dNTP mix, 35.5 µL of water and 1 µL of 50× Titanium Taq polymerase. The reaction mix was incubated at 95° C. for 1 minute followed by 35 cycles of 95° C. for 30 seconds, 55° C. for 15 seconds and 68° C. for 1 minute. A final and single incubation step at 68° C. for 10 minutes ended the thermal cycling program. Reaction vials containing the reaction mixture were either placed at 4° C. for short-term storage or at −20° C. for long-term storage.

Amplicon Purification

Amplicons were purified using Qiagen's MinElute PCR Purification Kit according to the manufacturer's instructions and eluted into 20 µL of elution buffer provided by Qiagen.

Amplicon Quantitation

Amplicons were quantitated using a Qubit Fluorometer and Qubit reagents from Life Technologies according to manufacturer's instructions.

Amplicon Visualization

Amplicons were visualized using E-Gel® EX agarose gels from Life Technologies according to manufacturer's instructions.

Results

Viral RNA was isolated from four clinical samples A, H, C, and D. After reverse transcription and amplification of a selected region of the viral genome using primers (HCV 1a 8068 $2^{nd}$ S (SEQ ID NO:63) and HCV 1a 8874 $2^{nd}$ AS (SEQ ID NO:35), 5 µL of the PCR mixture were combined with 15 µL of water and the entire volume of 20 µL was loaded onto a 2% E-Gel EX and analyzed. The observed amplicon sizes of all four samples were in good agreement with the expected length of the targeted region.

Conclusion

The targeted region in all four clinical samples was successfully amplified.

Example 2

PCR Amplification of Selected HCV Regions

This example describes PCR amplification of either plasmid DNA used in primer screening experiments or amplification of previously generated amplicons (nested PCR). The heterogeneity of the HCV viral genome and/or low titer concentrations require in most cases a subsequent 2nd or sometimes a 3rd PCR.

Materials

DNA was amplified using the Titanium® Taq PCR kit from Clontech (Mountain View, Calif., Catalog Number 639210).

Amplicons were purified using a MinElute PCR Purification Kit from Qiagen (Valencia, Calif., Catalog Number 28004).

Amplicons were quantitated on a Qubit® Fluorometer using Qubit® reagents from Life Technologies (Carlsbad, Calif., Catalog Numbers Q32866 and Q32851).

Amplicons were visualized on E-Gel® EX agarose gels from Life Technologies (Carlsbad, Calif., Catalog Number G 402002).

Cloned plasmid DNA or amplicons from previous PCR amplification reactions were used.

PCR amplification reactions were run on either Rotor Gene Q instruments from Qiagen (Valencia, Calif., Catalog Number 901560) or Veriti® Thermal Cyclers from Life Technologies (Carlsbad, Calif., Catalog Numbers 4375786).

Sense and antisense primer pairs used in PCR amplification reactions are shown in Table 1, below ("1a" and "1b" indicated either HCV-1a or HCV-1b as target nucleic acid; "A[#]" indicating one of seven target regions by number, and "1st," "2nd," or "3rd" indicating one of three primer sets used to amplify the indicated target region). Primer sequences that include a nucleotide base code other than A, C, T and G were synthesized to randomly couple a mixture of nucleobases at that non-ACTG nucleotide base code. For example, 5'-GCTCCRGGACTGCACCAT (SEQ ID NO:65) was synthesized so that at the R position, the oligonucleotide synthesizer randomly coupled a G or an A residue into the SEQ ID NO:65 primers. Primers were synthesized using an Expedite Synthesizer (Applied Biosystems, Carlsbad, Calif.), For nucleobases represented by a non-ACTG nucleotide base code, the Expedite system was programmed to draw equally from the containers of A, C, T or G, as represented by the nucleotide base code. The mixture of nucleobases were then added to the column and allowed to couple to the growing primer sequences. Using SEQ ID NO:65 as an example, to synthesize the R residue, the Expedite system drew equally from the G container and the A container to deposit a mixture of G and A in the column. Randomly, a G residue or an A residue would couple to the terminal G residue (primers were synthesized from 3' to 5') on each partially synthesized primer sequence in the column. In the next cycle, the C residue was coupled to either a G residue or an A residue, depending randomly on whether R was a G or an A for any given partial primer sequence in the column. The end result was a heterogeneous collection of primer sequences used as SEQ ID NO:65 primers.

TABLE 1

Sense and Antisense Primer Pairs for Amplification of Selected Regions of HCV-1a and HCV-1b

| Primer Set | Sense Primer-5'→3' (SEQ ID NO) | Antisense Primer-5'→3' (SEQ ID NO) |
|---|---|---|
| 1a A1 1st | GCTCCRGGACTGCACCAT (65) | GGTTGGGRARGAGGTAGATG (69) |
| 1a A1 2nd | TGCTCGTGTGYGGCGACGAC (43) | TACCCCTGCAGCRAGCAGGA (38) |
| 1a A1 3rd | CTTRGTCGTTATCTGTGARAG (34) | TAGGCARAACCAGAACCAGC (41) |
| 1a A2 1st | CAYTACCAGGACGTGCTYAAG (57) | TACCTGGTCATAGCCTCCGTGAA (40) |
| 1a A2 2nd | GCGGCGTCRAAAGTGAAGG (63) | GAAGGCTCTCAGGYTCGC (35) |
| 1a A2 3rd | AAGGCYAACYTGCTATCCGA (28) | TCGCYGCRTCCTCCTGGA (42) |
| 1a A3 1st | CCATCYCTCAARGCAACTTG (60) | CCACACGGAGTTGATGTGG (31) |
| 1a A3 2nd | CCAACCAYGACTCCCCTGA (58) | TACGGCCTTTCTGGCRTGGC (73) |
| 1a A3 3rd | GCYGAGCTCATAGARGCYAA (36) | GCARCGGACGTCYTTTGCC (62) |
| 1a A4 1st | CAGTGCARTGGATGAACCG (55) | AGCGGATCRAARGAGTCCA (46) |

TABLE 1-continued

Sense and Antisense Primer Pairs for Amplification of Selected Regions of HCV-1a and HCV-1b

| Primer Set | Sense Primer-5'→3' (SEQ ID NO) | Antisense Primer-5'→3' (SEQ ID NO) |
|---|---|---|
| 1a A4 2nd | GGYTRATAGCCTTCGCCTC (70) | ACCACTTTRTTCTCYGACTC (45) |
| 1a A4 3rd | CACTAYGTGCCRGAGAGCGA (29) | CTGGTRATRTTRCCGCCCAT (61) |
| 1a A5 1st | TACCTGGTAGCGTACCAAG (39) | ARCACCTCGCATATCCAGTC (47) |
| 1a A5 2nd | TGTGCGCTAGRGCYCAAGC (44) | CAGGARCCGGAGCAYGGAGT (51) |
| 1a A5 3rd | GGACCAGATGTGGAAGTGYT (68) | CCACTGRTGYAGTCGCCTCA (59) |
| 1a A6 1st | CAGGRGGYGCTTATGACATAAT (52) | GTCRGCCGACATRCATGTCATRAT (37) |
| 1a A6 2nd | ATAAYTTGTGAYGAGTGCCAC (49) | TTCATTCTGRACAGCRCCCA (75) |
| 1a A6 3rd | GTYCTTGACCARGCAGAGA (72) | CAGTCTGTATAGYAGRGGTGT (53) |
| 1a A7 1st | GTAYGCCCAGCAGACRAG (77) | GGGATAGCCTTGCCGTAAA (78) |
| 1a A7 2nd | GGGACAAAAACCARGTGGAG (79) | GATCTCTCCGGTRGTGGAC (80) |
| 1a A7 3rd | TGAGGTYCAGATYGTGTCAA (81) | GTTAGGRTGGGRCACRGTGA (71) |
| 1b A1 1st | TCCRGGACTGCACRATGCT (21) | TTGGGGAGCARGTAGATGCC (76) |
| 1b A1 2nd | TGCTCGTGTRCGGRGACGA (86) | TACCCCTACRGARAGTAGGA (87) |
| 1b A1 3rd | CCTYGTCGTTATCTGTGARAG (88) | TAGGCACMACATGAACCAGC (89) |
| 1b A2 1st | TACCRGGACGTGCTYAAGGAGA (82) | TACCTAGTCATAGCCTCCGTGAA (90) |
| 1b A2 2nd | AGGCGTCCACAGTYAAGGC (4) | GAAGACTCGTAGGYTCGC (92) |
| 1b A2 3rd | AAGGCTARACTYCTATCYGTAGA (2) | TCGCCGCRTCCTCYTG (91) |
| 1b A3 1st | TGAAGGCRACATGCACYACC (83) | CTTCCARCARGTCCTYCCAC (84) |
| 1b A3 2nd | TGCACYACCCRTCAYGACTC (24) | GGTTRACGGCCYTGCTGGATA (5) |
| 1b A3 3rd | GCYGACCTCATYGAGGCCAA (94) | GAYAGGYTCCGGACGTCCTT (12) |
| 1b A4 1st | GGCTGTGCARTGGATGAA (95) | AAGCGGRTCRAAAGAGTCYA (1) |
| 1b A4 2nd | ACCGGCTGATAGCGTTCGC (85) | CYACCTTRTTYTCTGACTCCAC (11) |
| 1b A4 3rd | CACTAYGTGCCTGARAGCGA (96) | GGGTGATGTTRCCGCCCAT (18) |
| 1b A5 1st | TACCTGGYAGCRTACCARGC (97) | GTCARCACCGTGCATATCCA (19) |
| 1b A5 2nd | TGTGCGCCAGGGCYCARGC (98) | ACGARCCGGAGCAYGGCGT (3) |
| 1b A5 3rd | GTGGGAYCARATGTGGAAGTG (99) | ATCCACTGGTGRAGCCTCTT (7) |
| 1b A6 1st | TCYGGGGGCGCCTAYGACAT (23) | GTCRGCCGACATGCATGCCATGAT (100) |
| 1b A6 2nd | CATCATAATATGYGATGAGTGCCA (8) | CCTCRTTTTGRACGGCTCC (10) |
| 1b A6 3rd | TGGAYCAAGCGGAGACGG (26) | CCTATACAGYAGGGGYGTTG (9) |
| 1b A7 1st | CGGCRTGYGGGGACATCAT (101) | GGGATGGCYTTGCCATARAA (17) |
| 1b A7 2nd | GGCCTACKCCCARCAGAC (15) | TGGACAGRGCYACCTCCT (74) |
| 1b A7 3rd | ATCATCACYAGCCTCACAGG (6) | TTRGGRTGTGGCACGGTRA (27) |

Methods

PCR Amplification

A volume of 2.5 µL of either plasmid DNA (1 ng/µL) or previously amplified DNA was combined with 47.5 µL of a mastermix consisting of 2.5 µL of PCR sense primer (10 µM), 2.5 µL of PCR anti-sense primer (10 µM), 5 µL of 10× Titanium Taq buffer, 1 µL of 50× dNTP mix, 35.5 µL of water and 1 µL of 50× Titanium Taq polymerase. The reaction mix was incubated at 95° C. for 1 minute followed by 35 cycles of 95° C. for 30 seconds, 55° C. for 15 seconds and 68° C. for 1 minute. A final and single incubation step at 68° C. for 10 minutes ended the thermal cycling program.

Reaction vials containing the reaction mixture were either placed at 4° C. for short-term storage or at −20° C. for long-term storage.

Amplicon Purification

Amplicons were purified using Qiagen's MinElute PCR Purification Kit according to the manufacturer's instructions and eluted into 20 µL of elution buffer provided by Qiagen.

Amplicon Quantitation

Amplicons were quantitated using a Qubit Fluorometer and Qubit reagents from Life Technologies according to manufacturer's instructions.

Amplicon Visualization

Amplicons were visualized using E-Gel® EX agarose gels from Life Technologies according to manufacturer's instructions.

Results

Selected regions of cloned regions of the HCV viral genome were amplified using primer pairs as shown in Table 1. For each target region (indicated as one of "A1" through "A7" in the Table), three different primer combinations were evaluated (indicated by "1st," "2nd," and "3rd"). Amplicons were purified and quantitated as described above. Purified amplicons were combined with water to a total volume of 20 µL, which was loaded onto a 2% E-Gel EX and analyzed. The observed amplicon sizes of the tested primer combinations were in good agreement with the expected length of the targeted region.

Conclusion

The targeted regions were successfully amplified using all three primer combinations for each of the HCV-1a and -1b target regions.

Example 3

SMRT Sequencing of Selected HCV Regions

This example describes SMRT sequencing results with respect to the entire NS3, NS4a, NS4b, NS5a, and NS5b regions of the HCV genome using a set of seven primer pairs and a HCV 1a reference sample.

Materials

DNA was amplified using the Titanium® Taq PCR kit from Clontech (Mountain View, Calif., Catalog Number 639210).

Amplicons were purified using a MinElute PCR Purification Kit from Qiagen (Valencia, Calif., Catalog Number 28004).

Amplicons were quantitated on a Qubit® Fluorometer using Qubit® reagents from Life Technologies (Carlsbad, Calif., Catalog Numbers Q32866 and Q32851).

Amplicons were visualized on E-Gel® EX agarose gels from Life Technologies (Carlsbad, Calif., Catalog Number G 402002).

PCR amplification reactions were run on either Rotor Gene Q instruments from Qiagen (Valencia, Calif., Catalog Number 901560) or Veriti® Thermal Cyclers from Life Technologies (Carlsbad, Calif., Catalog Numbers 4375786).

SMRTbell templates were prepared using DNA Template Prep Kit 2.0 kits from Pacific Biosciences (Menlo Park, Calif. Catalog number 001-322-716).

DNA Sequencing was performed on a Pacbio RS instrument using DNA Polymerase Binding Kits (Catalog number 001-359-802), SMRT Cell 8 Pacs (Catalog number 001-264-427) and DNA Sequencing Kits (Catalog Number 001-379-044) from Pacific Biosciences.

Sense and antisense primer pairs used in PCR amplification reactions are shown in Table 2, below. Primer sequences that include a nucleotide base code other than A, C, T and G were synthesized using a mixture of nucleobases, as described above.

TABLE 2

Sense and Primer Pairs for Amplification of Overlapping Amplicons from HCV-1a.

| Primer Set | Sense Primer (SEQ ID NO) | Antisense Primer (SEQ ID NO) |
| --- | --- | --- |
| Amplicon 1 | (65) | (69) |
| Amplicon 2 | (57) | TACCTVGTCATAGCCTCCGTGAA (184) |
| Amplicon 3 | (36) | (31) |
| Amplicon 4 | (55) | (61) |
| Amplicon 5 | (68) | GGGAGGCGAARGCTATYA (147) |
| Amplicon6 | (72) | (37) |
| Amplicon 7 | CAGCAGACRAGRGGYCT (120) | TGGACAGRGCRACCTCCT (25) |

Methods

Seven overlapping and approximately 1 kb long amplicons were generated from a HCV 1a reference sample using an amplification reaction as generally described in Example 2 and the primer pairs shown in Table 2. All individual amplicons were purified and quantitated as described earlier. The seven amplicons were mixed in equal amounts and a total amount of 1 µg of DNA was converted into SMRTbells according to the manufacturer's instructions with the exception that SMRTbell templates were purified three times instead of only two times in the last step. SMRTbell templates were then sequenced on the Pacbio RS instrument following the manufacturer's protocol. Data were analyzed using the manufacturer's primary and secondary analysis software package. Sequencing reads were mapped to the original reference sequence.

Results

Seven selected and amplified regions of a cloned HCV reference were mixed and sequenced in one run on the Pacbio RS instrument using the sequencing primer provided in the Pacific Biosciences sequencing kit.

The depth of coverage—i.e., how many times an individual position was sequenced using SMRT sequencing— was determined for the seven amplicon regions including the six overlapping regions. The mean depth of coverage was 14,493-fold.

Conclusion

The obtained high depth of coverage demonstrates successful amplification of the individual seven targeted regions and complete sequencing of the targeted 6 kb long HCV region without any gaps.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A method for determining at least partial genotype information for hepatitis C virus type 1b (HCV-1b) in a sample, the method comprising:
   (1) contacting a sample, said sample suspected of containing HCV-1b, with at least two amplification oligomers for amplifying at least one target region of an HCV-1b target nucleic acid, wherein said at least one HCV-1b target region is selected from the group consisting of
      (a) a first target region corresponding to nucleotide positions 8504 to 9350 of SEQ ID NO: 156, wherein if the first target region is amplified, then the at least two amplification oligomers comprise (i) at least one oligomer comprising a target-hybridizing sequence comprising a nucleotide sequence selected from SEQ ID NOs: 21, 86, and 88; and (ii) at least one oligomer comprising a target-hybridizing sequence comprising a nucleotide sequence selected from SEQ ID NOs: 76, 87, and 89;
      (b) a second target region corresponding to nucleotide positions 7771 to 8618 of SEQ ID NO: 156, wherein if the second target region is amplified, then the at least two amplification oligomers comprise (i) at least one oligomer comprising a target-hybridizing sequence comprising a nucleotide sequence selected from SEQ ID NOs: 82, 4, and 2; and (ii) at least one oligomer comprising a target-hybridizing sequence comprising a nucleotide sequence selected from SEQ ID NOs: 90, 92, and 91;
      (c) a third target region corresponding to nucleotide positions 6956 to 7966 of SEQ ID NO: 156, wherein if the third target region is amplified, then the at least two amplification oligomers comprise (i) at least one oligomer comprising a target-hybridizing sequence comprising a nucleotide sequence selected from SEQ ID NOs: 83, 24, and 94; and (ii) at least one oligomer comprising a target-hybridizing sequence comprising a nucleotide sequence selected from SEQ ID NOs: 84, 5, and 12;
      (d) a fourth target region corresponding to nucleotide positions 6057 to 7101 of SEQ ID NO: 156, wherein if the fourth target region is amplified, then the at least two amplification oligomers comprise (i) at least one oligomer comprising a target-hybridizing sequence comprising a nucleotide sequence selected from SEQ ID NOs: 95, 85, and 96; and (ii) at least one oligomer comprising a target-hybridizing sequence comprising a nucleotide sequence selected from SEQ ID NOs: 1, 11, and 18;
      (e) a fifth target region corresponding to nucleotide positions 5077 to 6290 of SEQ ID NO: 156, wherein if the fifth target region is amplified, then the at least two amplification oligomers comprise (i) at least one oligomer comprising a target-hybridizing sequence comprising a nucleotide sequence selected from SEQ ID NOs: 97, 98, and 99; and (ii) at least one oligomer comprising a target-hybridizing sequence comprising a nucleotide sequence selected from SEQ ID NOs: 19, 3, and 7;
      (f) a sixth target region corresponding to nucleotide positions 4240 to 5280 of SEQ ID NO: 156, wherein if the sixth target region is amplified, then the at least two amplification oligomers comprise (i) at least one oligomer comprising a target-hybridizing sequence comprising a nucleotide sequence selected from SEQ ID NOs: 23, 8, and 26; and (ii) at least one oligomer comprising a target-hybridizing sequence comprising a nucleotide sequence selected from SEQ ID NOs: 100, 10, and 9; and
      (g) a seventh target region corresponding to nucleotide positions 3296 to 4466 of SEQ ID NO:156, wherein if the seventh target region is amplified, then the at least two amplification oligomers comprise (i) at least one oligomer comprising a target-hybridizing sequence comprising a nucleotide sequence selected from SEQ ID NOs: 101, 15, and 6; and (ii) at least one oligomer comprising a target-hybridizing sequence comprising a nucleotide sequence selected from SEQ ID NOs: 17, 74, and 27;
   (2) performing at least one in vitro nucleic acid amplification reaction, wherein any HCV-1b target nucleic acid present in said sample is used as a template for generating at least one amplification product corresponding to at least one of the first through seventh target regions; and
   (3) detecting the nucleobase at one or more nucleotide positions within the at least one amplification product, thereby determining at least partial genotype information for the HCV-1b in said sample.

2. The method of claim 1, wherein
   the target-hybridizing sequence of the at least one amplification oligomer of (a)(i) consists of the target-hybridizing sequence selected from SEQ ID NOs: 21, 86, and 88;
   the target-hybridizing sequence of the at least one amplification oligomer of (a)(ii) consists of the target-hybridizing sequence selected from SEQ ID NOs: 76, 87, and 89;
   the target-hybridizing sequence of the at least one amplification oligomer of (b)(i) consists of the target-hybridizing sequence selected from SEQ ID NOs: 82, 4, and 2;
   the target-hybridizing sequence of the at least one amplification oligomer of (b)(ii) consists of the target-hybridizing sequence selected from SEQ ID NOs: 90, 92, and 91;

the target-hybridizing sequence of the at least one amplification oligomer of (c)(i) consists of the target-hybridizing sequence selected from SEQ ID NOs: 83, 24, and 94;

the target-hybridizing sequence of the at least one amplification oligomer of (c)(ii) consists of the target-hybridizing sequence selected from SEQ ID NOs: 84, 5, and 12;

the target-hybridizing sequence of the at least one amplification oligomer of (d)(i) consists of the target-hybridizing sequence selected from SEQ ID NOs: 95, 85, and 96;

the target-hybridizing sequence of the at least one amplification oligomer of (d)(ii) consists of the target-hybridizing sequence selected from SEQ ID NOs: 1, 11, and 18;

the target-hybridizing sequence of the at least one amplification oligomer of (e)(i) consists of the target-hybridizing sequence selected from SEQ ID NOs: 97, 98, and 99;

the target-hybridizing sequence of the at least one amplification oligomer of (e)(ii) consists of the target-hybridizing sequence selected from SEQ ID NOs: 19, 3, and 7;

the target-hybridizing sequence of the at least one amplification oligomer of (f)(i) consists of the target-hybridizing sequence selected from SEQ ID NOs: 23, 8, and 26;

the target-hybridizing sequence of the at least one amplification oligomer of (f)(ii) consists of the target-hybridizing sequence selected from SEQ ID NOs: 100, 10, and 9;

the target-hybridizing sequence of the at least one amplification oligomer of (g)(i) consists of the target-hybridizing sequence selected from SEQ ID NOs: 101, 15, and 6; and/or the target-hybridizing sequence of the at least one amplification oligomer of (g)(ii) consists of the target-hybridizing sequence selected from SEQ ID NOs: 17, 74, and 27.

3. The method of claim 1, where the detecting step comprises sequencing the at least one amplification product.

4. The method of claim 3, wherein said sequencing comprises single molecule real time (SMRT) sequencing.

5. The method of claim 1, wherein the detecting step comprises detecting, in a hybridization assay, an ability of the at least one amplification product to hybridize to a SNP-specific probe oligomer.

6. The method of claim 1, wherein the detecting step comprises detecting, in an amplification-based assay, an ability of a SNP-specific amplification oligomer to amplify a region of the at least one amplification product.

7. The method of claim 1, wherein the at least one in vitro amplification reaction comprises at least one of an RT-PCR amplification reaction and a PCR amplification reaction.

8. The method of claim 1, wherein the method further comprises contacting the sample with at least one capture probe oligomer comprising a nucleotide sequence that hybridizes to the HCV-1b target nucleic acid, wherein the at least one capture probe further comprises a nucleotide sequence or moiety that binds to an immobilized probe.

9. The method of claim 1, wherein each of said first through seventh target regions are amplified to produce at least one amplification product corresponding to each of said target regions, and wherein the detecting step comprises detecting the nucleobase at one or more positions within each of said amplification products.

10. The method of claim 9, wherein the contacting step comprises contacting the sample with all of the oligomers of (a)(i); all of the oligomers of (a)(ii); all of the oligomers of (b)(i); all of the oligomers of (b)(ii); all of the oligomers of (c)(i); all of the oligomers of (c)(ii); all of the oligomers of (d)(i); all of the oligomers of (d)(ii); all of the oligomers of (e)(i); all of the oligomers of (e)(ii); all of the oligomers of (f)(i); all of the oligomers of (f)(ii); all of the oligomers of (g)(i); and all of the oligomers of (g)(ii).

* * * * *

SEQUENCE LISTING

```
<160> NUMBER OF SEQ ID NOS: 184

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 1
aagcggrtcr aaagagtcya                                                    20

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 2
aaggctarac tyctatcygt aga                                                23

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 3
acgarccgga gcayggcgt                                                     19

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 4
aggcgtccac agtyaaggc                                                     19

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 5
ggttracggc cytgctggat a                                                  21

<210> SEQ ID NO 6
<211> LENGTH: 20
<212> TYPE: DNA
<213> ORGANISM: Artificial Sequence
<220> FEATURE:
```

<223> OTHER INFORMATION: Synthetic Oligomer

<400> SEQUENCE: 6
atcatcacya gcctcacagg                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 7
atccactggt gragcctctt                                    20

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 8
catcataata tgygatgagt gcca                               24

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 9
cctatacagy aggggygttg                                    20

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 10
cctcrttttg racggctcc                                     19

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 11
cyaccttrtt ytctgactcc ac                                 22

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 12
gayaggytcc ggacgtcctt                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 13
gccgagctca tagaggctaa                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 14
gccgagctca tagargcyaa                                               20

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 15
ggcctackcc carcagac                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 16
ggcygtrcar tggatgaa                                                 18

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 17
gggatggcyt tgccataraa                                               20

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 18
gggtgatgtt rccgcccat                                                19

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligomer

```
<400> SEQUENCE: 19
gtcarcaccg tgcatatcca                                           20

<210> SEQ ID NO 20
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 20
gtgggaycar atgtggaart g                                         21

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 21
tccrggactg cacratgct                                            19

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 22
tctgcgcctt cyttgaaggc                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 23
tcygggggcg cctaygacat                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 24
tgcacyaccc rtcaygactc                                           20

<210> SEQ ID NO 25
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 25
tggacagrgc racctcct                                             18

<210> SEQ ID NO 26
<211> LENGTH: 18
```

```
<212> TYPE: DNA
<213> ORGANISM: Artificial Sequence
<220> FEATURE:
<223> OTHER INFORMATION: Synthetic Oligomer

<400> SEQUENCE: 26
tggaycaagc ggagacgg                                                 18

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 27
ttrggrtgtg gcacggtra                                                19

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 28
aaggcyaacy tgctatccga                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 29
cactaygtgc crgagagcga                                               20

<210> SEQ ID NO 30
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 30
carcagacrc ggggyct                                                  17

<210> SEQ ID NO 31
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 31
ccacacggag ttgatgtgg                                                19

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 32
```
ccacacggag ykgatgtgg                                                   19

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 33
ccgcrtgcgg ygacatcatc                                                  20

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 34
cttrgtcgtt atctgtgara g                                                21

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 35
gaaggctctc aggytcgc                                                    18

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 36
gcygagctca tagargcyaa                                                  20

<210> SEQ ID NO 37
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 37
gtcrgccgac atrcatgtca trat                                             24

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 38 taccectgca gcragcagga                                                  20

<210> SEQ ID NO 39
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 39
tacctggtag cgtaccaag                                        19

<210> SEQ ID NO 40
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 40
tacctggtca tagcctccgt gaa                                   23

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 41
taggcaraac cagaaccagc                                       20

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 42
tcgcygcrtc ctcctgga                                         18

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 43
tgctcgtgtg yggcgacgac                                       20

<210> SEQ ID NO 44
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 44
tgtgcgctag rgcycaagc                                        19

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 45
accactttrt tctcygactc                                       20

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 46
agcggatcra argagtcca                                                  19

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 47
arcacctcgc atatccagtc                                                 20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 48
ataatyacca gcytgacygg                                                 20

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 49
ataayttgtg aygagtgcca c                                               21

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 50
atagccttgc crtaaaargg                                                 20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 51
caggarccgg agcayggagt                                                 20

<210> SEQ ID NO 52
<211> LENGTH: 22
<212> TYPE: DNA
<213> ORGANISM: Artificial Sequence
<220> FEATURE:
<223> OTHER INFORMATION: Synthetic Oligomer

```
<400> SEQUENCE: 52
caggrggygc ttatgacata at                                              22

<210> SEQ ID NO 53
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 53
cagtctgtat agyagrggtg t                                               21

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 54
cagtgcaatg gatgaaccg                                                  19

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 55
cagtgcartg gatgaaccg                                                  19

<210> SEQ ID NO 56
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 56
cattaccagg acgtgctcaa g                                               21

<210> SEQ ID NO 57
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 57
caytaccagg acgtgctyaa g                                               21

<210> SEQ ID NO 58
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 58
ccaaccayga ctccccctga                                                 19

<210> SEQ ID NO 59
```

```
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 59
ccactgrtgy agtcgcctca                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 60
ccatcyctca argcaacttg                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 61
ctggtratrt trccgcccat                                              20

<210> SEQ ID NO 62
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 62
gcarcggacg tcytttgcc                                               19

<210> SEQ ID NO 63
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 63
gcggcgtcra aagtgaagg                                               19

<210> SEQ ID NO 64
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 64
gctccaggac tgcaccat                                                18

<210> SEQ ID NO 65
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 65
```

```
gctccrggac tgcaccat                                          18

<210> SEQ ID NO 66
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 66
gctccrgrac tgcaccat                                          18

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 67
ggaccagatg tggaagtgct                                        20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 68
ggaccagatg tggaagtgyt                                        20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 69
ggttgggrar gaggtagatg                                        20

<210> SEQ ID NO 70
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 70
ggytratagc cttcgcctc                                         19

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 71
gttaggrtgg grcacrgtga                                        20

<210> SEQ ID NO 72
<211> LENGTH: 19
<212> TYPE: DNA
```

<213> ORGANISM: Artificial Sequence
<220> FEATURE:
<223> OTHER INFORMATION: Synthetic Oligomer

<400> SEQUENCE: 72
gtycttgacc argcagaga                                                19

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 73
tacggccttt ctggcrtggc                                               20

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 74
tggacagrgc yacctcct                                                 18

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 75
ttcattctgr acagcrccca                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 76
ttggggagca rgtagatgcc                                               20

<210> SEQ ID NO 77
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 77
gtaygcccag cagacrag                                                 18

<210> SEQ ID NO 78
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 78
gggatagcct tgccgtaaa                                                19

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 79
gggacaaaaa ccargtggag                                               20

<210> SEQ ID NO 80
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 80
gatctctccg gtrgtggac                                                19

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 81
tgaggtycag atygtgtcaa                                               20

<210> SEQ ID NO 82
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 82
taccrggacg tgctyaagga ga                                            22

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 83
tgaaggcrac atgcacyacc                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 84
cttccarcar gtcctyccac                                               20

<210> SEQ ID NO 85
<211> LENGTH: 19
<212> TYPE: DNA
<213> ORGANISM: Artificial Sequence
<220> FEATURE:

<223> OTHER INFORMATION: Synthetic Oligomer

<400> SEQUENCE: 85
accggctgat agcgttcgc                                                19

<210> SEQ ID NO 86
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 86
tgctcgtgtr cggrgacga                                                19

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 87
tacccctacr garagtagga                                               20

<210> SEQ ID NO 88
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 88
cctygtcgtt atctgtgara g                                             21

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 89
taggcacmac atgaaccagc                                               20

<210> SEQ ID NO 90
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 90
tacctagtca tagcctccgt gaa                                           23

<210> SEQ ID NO 91
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 91
tcgccgcrtc ctcytg                                                   16

```
<210> SEQ ID NO 92
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 92
gaagactcgt aggytcgc                                                   18

<210> SEQ ID NO 93
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 93
ggttgacggc cytgctggat a                                               21

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 94
gcygacctca tygaggccaa                                                 20

<210> SEQ ID NO 95
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 95
ggctgtgcar tggatgaa                                                   18

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 96
cactaygtgc ctgaragcga                                                 20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 97
tacctggyag crtaccargc                                                 20

<210> SEQ ID NO 98
<211> LENGTH: 19
<212> TYPE: DNA
<213> ORGANISM: Artificial Sequence
<220> FEATURE:
<223> OTHER INFORMATION: Synthetic Oligomer
```

<400> SEQUENCE: 98
tgtgcgccag ggcycargc                                              19

<210> SEQ ID NO 99
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 99
gtgggaycar atgtggaagt g                                           21

<210> SEQ ID NO 100
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 100
gtcrgccgac atgcatgcca tgat                                        24

<210> SEQ ID NO 101
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 101
cggcrtgygg ggacatcat                                              19

<210> SEQ ID NO 102
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 102
aagtccaaga ggaccccat                                              19

<210> SEQ ID NO 103
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 103
acggagttga tgtggkyta                                              19

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 104
acggagttga tgtggkytac                                             20

<210> SEQ ID NO 105
<211> LENGTH: 20

```
<212> TYPE: DNA
<213> ORGANISM: Artificial Sequence
<220> FEATURE:
<223> OTHER INFORMATION: Synthetic Oligomer

<400> SEQUENCE: 105
acgtggaaat aaggcaggtg                                            20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 106
acgtggarat aaggcrggtg                                            20

<210> SEQ ID NO 107
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 107
acyggccggg ayaaraa                                               17

<210> SEQ ID NO 108
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 108
acytgcggct cctcrgat                                              18

<210> SEQ ID NO 109
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 109
agatgggcgg raacatcac                                             19

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 110
agcacctcgc atatccagtc                                            20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 111
```

```
agccttgacc cyacyttyac                                          20
```

<210> SEQ ID NO 112
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 112

```
aggtcatcac ccctgctgt                                           19
```

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 113

```
atccttgtgg acatccttgc                                          20
```

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 114

```
atcracggcy tgcccgtytc                                          20
```

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 115

```
atgggaagct cctacggrtt                                          20
```

<210> SEQ ID NO 116
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 116

```
attgaccagg tcctctgt                                            18
```

<210> SEQ ID NO 117
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 117

```
caacagacaa ggggcct                                             17
```

<210> SEQ ID NO 118
<211> LENGTH: 20
<212> TYPE: DNA
<213> ORGANISM: Artificial Sequence

```
<220> FEATURE:
<223> OTHER INFORMATION: Synthetic Oligomer

<400> SEQUENCE: 118
cactaccagg acgtgctcaa                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 119
cagaaggcct cgagtttttg                                              20

<210> SEQ ID NO 120
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 120
cagcagacra grggyct                                                 17

<210> SEQ ID NO 121
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 121
cargcrgara cggctgga                                                18

<210> SEQ ID NO 122
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 122
ccatgaatca ctcccctgtg ag                                           22

<210> SEQ ID NO 123
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 123
ccatytgcac gtartgrcc                                               19

<210> SEQ ID NO 124
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 124
ccgagcgggg accaaaaaga t                                            21
```

<210> SEQ ID NO 125
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 125
cctcacytgy tacatcaagg c                                      21

<210> SEQ ID NO 126
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 126
cgagcaggca gcaggaagat g                                      21

<210> SEQ ID NO 127
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 127
cgagcgggga gtaaaaagat g                                      21

<210> SEQ ID NO 128
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 128
cgctraggcc atggagtct                                         19

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 129
cggttgggra rgaggtagat                                        20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 130
cggttgggra rgaggtarat                                        20

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 131
ctggtgatgt tgccgcccat                                        20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 132
gacagrgcra cctcctcrat                                        20

<210> SEQ ID NO 133
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 133
gaggcgactr caycagtgg                                         19

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 134
gcaacctcct cgatgttagg                                        20

<210> SEQ ID NO 135
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 135
gcctgcyact ccatagaa                                          18

<210> SEQ ID NO 136
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 136
gcctgcyact ccatagaac                                         19

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 137
gcctgcyact ccatagaacc                                        20

<210> SEQ ID NO 138

```
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 138
gcggagtacc tggtcatagc                                                 20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 139
gcrgartacc tggtcatagc                                                 20

<210> SEQ ID NO 140
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 140
gctygtggac atyctrgc                                                   18

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 141
gcygagcagt tcaarcagaa                                                 20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 142
gcygagctca tagaggcyaa                                                 20

<210> SEQ ID NO 143
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 143
ggcagaactg yggytatcg                                                  19

<210> SEQ ID NO 144
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 144
```
ggcatggaag aacaggactc                                          20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 145
ggcatggarg aayaggactc                                          20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 146
ggcctcctag ggtgcataat                                          20

<210> SEQ ID NO 147
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 147
gggaggcgaa rgctatya                                            18

<210> SEQ ID NO 148
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 148
gggcctrctt ggytgyat                                            18

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 149
ggtgttcatg taygctcgya                                          20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 150
ggttggggag gaggtagatg                                          20

<210> SEQ ID NO 151
<211> LENGTH: 19
<212> TYPE: DNA

<213> ORGANISM: Artificial Sequence
<220> FEATURE:
<223> OTHER INFORMATION: Synthetic Oligomer

<400> SEQUENCE: 151
ggttgggrar gaggtagat                                                    19

<210> SEQ ID NO 152
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 152
ggytgyatca tcacyag                                                      17

<210> SEQ ID NO 153
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 153
gtcaaagcag cgggtatcat                                                   20

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 154
gtcaaarcar cgggtrtcat                                                   20

<210> SEQ ID NO 155
<211> LENGTH: 9646
<212> TYPE: DNA
<213> ORGANISM: Hepatitis C virus
<300> PUBLICATION INFORMATION:
<308> DATABASE ACCESSION NUMBER: AF009606.1; GI:2316097
<309> DATABASE ENTRY DATE: 1997-08-09
<313> RELEVANT RESIDUES IN SEQ ID NO: (1)..(9646)

<400> SEQUENCE: 155
gccagccccc tgatggggc gacactccac catgaatcac tcccctgtga ggaactactg        60
tcttcacgca gaaagcgtct agccatggcg ttagtatgag tgtcgtgcag cctccaggac       120 ccccctccc gggagagcca tagtggtctg cggaaccggt gagtacaccg gaattgccag        180
gacgaccggg tcctttcttg gataaacccg ctcaatgcct ggagatttgg gcgtgccccc       240
gcaagactgc tagccgagta gtgttgggtc gcgaaaggcc ttgtggtact gcctgatagg       300
gtgcttgcga gtgccccggg aggtctcgta gaccgtgcac catgagcacg aatcctaaac       360
ctcaaagaaa aaccaaacgt aacaccaacc gtcgcccaca ggacgtcaag ttcccgggtg       420
gcggtcagat cgttggtgga gtttacttgt tgccgcgcag gggccctaga ttgggtgtgc       480
gcgcgacgag gaagacttcc gagcggtcgc aacctcgagg tagacgtcag cctatcccca       540
aggcacgtcg gccgagggc aggacctggg ctcagcccgg gtaccttggg cccctctatg       600
gcaatgaggg ttgcggtgg gcgggatggc tcctgtctcc ccgtggctct cggcctagct       660
ggggccccac agaccccgg cgtaggtcgc gcaatttggg taaggtcatc gataccctta       720

```
cgtgcggctt cgccgacctc atggggtaca taccgctcgt cggcgcccct cttggaggcg      780
ctgccagggc cctggcgcat ggcgtccggg ttctggaaga cggcgtgaac tatgcaacag      840
ggaaccttcc tggttgctct ttctctatct tccttctggc cctgctctct tgcctgactg      900
tgcccgcttc agcctaccaa gtgcgcaatt cctcggggct ttaccatgtc accaatgatt      960
gccctaactc gagtattgtg tacgaggcgg ccgatgccat cctgcacact ccggggtgtg     1020
tcccttgcgt tcgcgagggt aacgcctcga ggtgttgggt ggcggtgacc ccacggtgg      1080 ccaccaggga cggcaaactc cccacaacgc agcttcgacg tcatatcgat ctgcttgtcg     1140
ggagcgccac cctctgctcg gccctctacg tgggggacct gtgcgggtct gtctttcttg     1200
ttggtcaact gtttaccttc tctcccaggc gccactggac gacgcaagac tgcaattgtt     1260
ctatctatcc cggccatata acgggtcatc gcatggcatg ggatatgatg atgaactggt     1320
cccctacggc agcgttggtg gtagctcagc tgctccggat cccacaagcc atcatggaca     1380
tgatcgctgg tgctcactgg ggagtcctgg cgggcatagc gtatttctcc atggtgggga     1440
actgggcgaa ggtcctggta gtgctgctgc tatttgccgg cgtcgacgcg gaaacccacg     1500
tcaccggggg aagtgccggc cgcaccacgg ctgggcttgt tggtctcctt acaccaggcg     1560
ccaagcagaa catccaactg atcaacacca acggcagttg gcacatcaat agcacggcct     1620
tgaactgcaa tgaaagcctt aacaccggct ggttagcagg gctcttctat cagcacaaat     1680
tcaactcttc aggctgtcct gagaggttgg ccagctgccg acgccttacc gattttgccc     1740
agggctgggg tcctatcagt tatgccaacg gaagcggcct cgacgaacgc ccctactgct     1800
ggcactaccc tccaagacct tgtggcattg tgcccgcaaa gagcgtgtgt ggcccggtat     1860
attgcttcac tcccagcccc gtggtggtgg gaacgaccga caggtcgggc gcgcctacct     1920
acagctgggg tgcaaatgat acggatgtct tcgtccttaa caacaccagg ccaccgctgg     1980
gcaattggtt cggttgtacc tggatgaact caactggatt caccaaagtg tgcggagcgc     2040
ccccttgtgt catcggaggg gtgggcaaca acaccttgct ctgccccact gattgtttcc     2100
gcaagcatcc ggaagccaca tactctcggt gcggctccgg tcctggatt acacccaggt     2160 gcatggtcga ctaccgtat aggctttggc actatccttg taccatcaat tacaccatat     2220
tcaaagtcag gatgtacgtg ggaggggtcg agcacaggct ggaagcggcc tgcaactgga     2280
cgcggggcga acgctgtgat ctggaagaca gggacaggtc cgagctcagc ccattgctgc     2340
tgtccaccac acagtggcag gtccttccgt gttctttcac gaccctgcca gccttgtcca     2400
ccggcctcat ccacctccac cagaacattg tggacgtgca gtacttgtac ggggtagggt     2460
caagcatcgc gtcctgggcc attaagtggg agtacgtcgt tctcctgttc ctcctgcttg     2520
cagacgcgcg cgtctgctcc tgcttgtgga tgatgttact catatcccaa gcggaggcgg     2580
ctttggagaa cctcgtaata ctcaatgcag catccctggc cggacgcac ggtcttgtgt      2640 ccttcctcgt gttcttctgc tttgcgtggt atctgaaggg taggtgggtg cccggagcgg     2700
tctacgcctt ctacgggatg tggcctctcc tcctgctcct gctggcgttg cctcagcggg     2760
catacgcact ggacacggag gtggccgcgt cgtgtggcgg cgttgttctt gtcgggttaa     2820
tggcgctgac tctgtcgcca tattacaagc gctacatcag ctggtgcatg tggtggcttc     2880
agtattttct gaccagagta gaagcgcaac tgcacgtgtg ggttcccccc ctcaacgtcc     2940
ggggggggcg cgatgccgtc atcttactca tgtgtgttgt acacccgact ctggtatttg     3000
acatcaccaa actactcctg gccatcttcg gaccccttg gattcttcaa gccagtttgc     3060
```

```
ttaaagtccc ctacttcgtg cgcgttcaag gccttctccg gatctgcgcg ctagcgcgga    3120
agatagccgg aggtcattac gtgcaaatgg ccatcatcaa gttagggggcg cttactggca   3180
cctatgtgta taaccatctc accccctcttc gagactgggc gcacaacggc ctgcgagatc   3240
tggccgtggc tgtggaacca gtcgtcttct cccgaatgga gaccaagctc atcacgtggg    3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg    3420
cgcccatcac ggcgtacgcc cagcagacga gaggcctcct agggtgtata atcaccagcc    3480
tgactggccg ggacaaaaac caagtggagg gtgaggtcca gatcgtgtca actgctaccc    3540
aaaccttcct ggcaacgtgc atcaatgggg tatgctggac tgtctaccac ggggccggaa    3600
cgaggaccat cgcatcaccc aagggtcctg tcatccagat gtataccaat gtggaccaag    3660
accttgtggg ctggcccgct cctcaaggtt cccgctcatt gacaccctgc acctgcggct    3720
cctcggacct ttacctggtc acgaggcacg ccgatgtcat tcccgtgcgc cggcgaggtg    3780
atagcagggg tagcctgctt tcgccccggc ccatttccta cttgaaaggc tcctcggggg    3840
gtccgctgtt gtgccccgcg ggacacgccg tgggcctatt cagggccgcg gtgtgcaccc    3900
gtggagtggc taaggcggtg gactttatcc ctgtggagaa cctagagaca accatgagat    3960
ccccggtgtt cacggacaac tcctctccac cagcagtgcc ccagagcttc caggtggccc    4020
acctgcatgc tcccaccggc agcggtaaga gcaccaaggt cccggctgcg tacgcagccc    4080
agggctacaa ggtgttggtg ctcaacccct ctgttgctgc aacgctgggc tttggtgctt    4140
acatgtccaa ggcccatggg gttgatccta atatcaggac cggggtgaga acaattacca    4200
ctggcagccc catcacgtac tccacctacg gcaagttcct tgccgacggc gggtgctcag    4260
gaggtgctta tgacataata atttgtgacg agtgccactc cacggatgcc acatccatct    4320
tgggcatcgg cactgtcctt gaccaagcag agactgcggg ggcgagactg gttgtgctcg    4380
ccactgctac ccctccgggc tccgtcactg tgtcccatcc taacatcgag gaggttgctc    4440
tgtccaccac cggagagatc ccttttttacg gcaaggctat ccccctcgag gtgatcaagg    4500
ggggaagaca tctcatcttc tgccactcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca gacagtcgat ttcagccttg    4740
accctacctt taccattgag acaaccacgc tcccccagga tgctgtctcc aggactcaac    4800
gccggggcag gactggcagg gggaagccag gcatctacag atttgtggca ccgggggagc    4860
gcccctccgg catgttcgac tcgtccgtcc tctgtgagtg ctatgacgcg ggctgtgctt    4920
ggtatgagct cacgcccgcc gagactacag ttaggctacg agcgtacatg aacacccccgg    4980
ggcttcccgt gtgccaggac catcttgaat tttgggaggg cgtctttacg gcctcactc    5040
atatagatgc ccactttcta tcccagacaa agcagagtgg ggagaacttt ccttacctgg    5100
tagcgtacca agccaccgtg tgcgctaggg ctcaagcccc tcccccatcg tgggaccaga    5160
tgtggaagtg tttgatccgc cttaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat tgcctgtcaa caggctgcgt ggtcatagtg ggcaggattg    5400
tcttgtccgg gaagccggca attatacctg acagggaggt tctctaccag gagttcgatg    5460
```

```
agatggaaga gtgctctcag cacttaccgt acatcgagca agggatgatg ctcgctgagc    5520
agttcaagca gaaggccctc ggcctcctgc agaccgcgtc ccgccaagca gaggttatca    5580
cccctgctgt ccagaccaac tggcagaaac tcgaggtctt ctgggcgaag cacatgtgga    5640
atttcatcag tgggatacaa tacttggcgg gcctgtcaac gctgcctggt aaccccgcca    5700
ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ccgcctttgt gggcgctggc ttagctggcg ccgccatcgg cagcgttgga ctggggaagg    5880
tcctcgtgga cattcttgca gggtatgcgc cgggcgtggc gggagctctt gtagcattca    5940
agatcatgag cggtgaggtc ccctccacgg aggacctggt caatctgctg cccgccatcc    6000
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
cctttgtgtc ctgccagcgc gggtataggg ggtctggcg aggagacggc attatgcaca    6420
ctcgctgcca ctgtggagct gagatcactg gacatgtcaa aaacgggacg atgaggatcg    6480
tcggtcctag gacctgcagg aacatgtgga gtgggacgtt ccccattaac gcctacacca    6540
cgggcccctg tactcccctt cctgcgccga actataagtt cgcgctgtgg agggtgtctg    6600
cagaggaata cgtggagata aggcgggtgg gggacttcca ctacgtatcg ggtatgacta    6660
ctgacaatct taaatgcccg tgccagatcc catcgcccga atttttcaca gaattggacg    6720
gggtgcgcct acataggttt gcgccccctt gcaagccctt gctgcgggag gaggtatcat    6780
tcagagtagg actccacgag taccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcacccccit ctatggccag ctcctcggcc agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acccgcagaa attctgcgga agtctcggag attcgcccgg ccctgcccg    7200 tttgggcgcg gccggactac aaccccccgc tagtagagac gtggaaaaag cctgactacg    7260
aaccacctgt ggtccatggc tgcccgctac cacctccacg gtcccctcct gtgcctccgc    7320
ctcggaaaaa gcgtacggtg gtcctcaccg aatcaaccct atctactgcc ttggccgagc    7380
ttgccaccaa aagttttggc agctcctcaa cttccggcat tacgggcgac aatacgacaa    7440
catcctctga gcccgccect tctggctgcc ccccgactc cgacgttgag tcctattctt    7500
ccatgccccc cctggagggg gagcctgggg atccggatct cagcgacggg tcatggtcga    7560
cggtcagtag tggggccgac acggaagatg tcgtgtgctg ctcaatgtct tattcctgga    7620
caggcgcact cgtcacccc tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
```

```
tgctcaagga ggtcaaagca gcggcgtcaa aagtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
ttcagcctga aaggggggt cgtaagccag ctcgtctcat cgtgttcccc gacctgggcg     8100
tgcgcgtgtg cgagaagatg gccctgtacg acgtggttag caagctcccc ctggccgtga    8160
tgggaagctc ctacggattc caatactcac caggacagcg ggttgaattc ctcgtgcaag    8220
cgtggaagtc caagaagacc ccgatggggt tctcgtatga tacccgctgt tttgactcca    8280
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacaccctc acttgctaca tcaaggcccg gcagcctgt cgagccgcag    8520
ggctccagga ctgcaccatg ctcgtgtgtg gcgacgactt agtcgttatc tgtgaaagtg    8580
cggggtcca ggaggacgcg gcgagcctga gagccttcac ggaggctatg accaggtact    8640
ccgccccccc cggggaccccc ccacaaccag aatacgactt ggagcttata acatcatgct    8700
cctccaacgt gtcagtcgcc cacgacggcg ctggaaagag ggtctactac cttacccgtg    8760
accctacaac cccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacggagc ctgctactcc atagaaccac tggatctacc tccaatcatt caaagactcc    9000
atgggcctcag cgcatttca ctccacagtt actctccagg tgaaatcaat agggtggccg    9060
catgcctcag aaaacttggg gtcccgcccc tgcgagcttg agacaccgg gcccggagcg    9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggttg gttcacggct ggctacagcg gggagacat ttatcacagc gtgtctcatg    9300
cccggccccg ctggttctgg ttttgcctac tcctgctcgc tgcaggggta ggcatctacc    9360
tcctccccaa ccgatgaagg ttggggtaaa cactccggcc tcttaggcca tttcctgttt    9420
ttttttttt ttttttttt ttttttttt ttttttttt ttttttttct tttttttttt         9480
ttttttcctt ttttttttt tttttttct ttccttcttt tttccttttct tttccttcct    9540
tctttaatgg tggctccatc ttagccctag tcacggctag ctgtgaaagg tccgtgagcc    9600
gcatgactgc agagagtgct gatactggcc tctctgcaga tcatgt                   9646
```

<210> SEQ ID NO 156
<211> LENGTH: 9379
<212> TYPE: DNA
<213> ORGANISM: Hepatitis C virus
<300> PUBLICATION INFORMATION:
<308> DATABASE ACCESSION NUMBER: AJ000009.1; GI:2764397
<309> DATABASE ENTRY DATE: 1998-01-10
<313> RELEVANT RESIDUES IN SEQ ID NO: (1)..(9379)

<400> SEQUENCE: 156

```
ggcgacactc caccatagat cactcccctg tgaggaacta ctgtcttcac gcagaaagcg      60
tctagccatg gcgttagtat gagtgtcgtg cagcctccag acccccccct cccgggagag     120
ccatagtggt ctgcggaacc ggtgagtaca ccggaattgc caggacgacc gggtcctttc     180
```

```
ttggatcaac ccgctcaatg cctggagatt tgggcgtgcc cccgcgagac tgctagccga    240
gtagtgttgg gtcgcgaaag gccttgtggt actgcctgat agggtgcttg cgagtgcccc    300
gggaggtctc gtagaccgtg caccatgagc acgaatccta aacctcaaag aaaaaccaaa    360
cgtaacacca accgccgtcc acaggacgtc aagttcccgg gcggtggtca gatcgttggt    420
ggagtttacc tgttgccgcg caggggcccc aggttgggtg tgcgcgcgct caggaagact    480
tccgagcggt cgcaacctcg tgaaggcgaa caacctatcc ccaaggctcg ccgacccgag    540
ggcagggcct gggctcagcc cgggtaccct tggcccctct atggcaatga gggcatgggg    600
tgggcaggat ggctcctgtc accccgtggt tctcggccta gttggggccc ctcagacccc    660
cggcgtaggt cgcgtaattt gggtaaggtc atcgataccc ttacatgcgg cttcgccgac    720
ctcatggggt acattccgct cgtcggcgcc cctctagggg cgccgccag ggccctggcg     780 catggcgtcc gggttctgga ggacggcgtg aactatgcaa cagggaattt gcccggttgc    840
tctttctcta tcttcctctt gggttgctg tcttgtttga ccatcccagc ttccgcttat     900
gaagtgcgca acgtgtccgg ggtgtaccat gtcacgaacg actgctccaa cgcaagcatt    960
gtgtatgagg cagcggacat gatcatgcac gtccccgggt gcgtgccctg cgttcgggtg    1020
gacaactcct cccgttgctg ggtagcgctc accccacgc ttgcggccag gaacgctagc     1080
gtccctacta cggcaatacg acgccacgtc gatttgctcg ttggggcggc tactttctgt    1140
tccgctatgt acgtggggga tctctgcgga tctgttttcc tcgtcgccca gctgttcacc    1200
ttctcgcccc gccggcatga gacggtacag gactgcaatt gttcaatcta tcccggccac    1260
ataacgggtc accgcatggc ttgggatatg atgatgaact ggtcacccac agcagcccta    1320
gtcgtatcgc agttactccg gatcccacaa gctatcgtgg atatggtggc ggggccccac    1380
tggggagtcc tggcgggcct cgcctactat tccatggtgg ggaactgggc taaggttttg    1440
attgtgatgc tactctttgc cggcgttgac ggggacaccc acacgacggg ggggtggcg     1500 ggccgcgaca cgctgcgctt cacggggttc ttttcattgg ggccgaaaca aaagatccag    1560
cttgtaaaca ccaacggcag ctggcacatc aacaggactg ccctgaactg caatgactcc    1620
ctcaacactg gtggctcgc cgcgctgttc tacacacaca gcttcaacgc gtctggatgc    1680
ccagagcgga tggccagctg ccaccccatc gacgagttcg ctcaggggtg gtcccatt     1740 acttacgctg aacatagcag ctcggaccag aggccctact gttggcacta cgcacctcag    1800
ccgtgcggta ttgtacccgc gtcggaggtg tgtggtccag tgtattgctt caccccaagc    1860
cctgttgtgg tggggacaac cgatcgtcac ggcgtcccta cgtatagctg gggggagaat    1920
gggacggacg tgctgcttct caacaacacg cggccgccgc aaggcaactg gttcggctgt    1980
acatggatga acgcactgg gttcaccaag acgtgcgggg ccccccgtg taacatcggg     2040 ggggtcggca caacacccct gacctgcccc acggactgct tccggaagca ccccgaggcc    2100
acttacacca aatgcggctc ggggcccttg gttgacaccta ggtgcatggt tgactaccca    2160
tacaggctct ggcactaccc ctgcactgtc aacttcacca tctttaaggt taggatgtat    2220 gtgggggggcg tggaacacag gctcagcgcc gcatgcaatt ggactcgagg agagcgttgt    2280
gacctggagg acagggatag atcagagctt agcccgctgc tgctgtccac aacagagtgg    2340
caggtgctgc cctgttcctt caccaccca ccggctctgt ccactggttt gatccatctc     2400
caccagaaca tcgtggacgt gcaatacttg tacggtatag gtcggtggt tgtctccttt    2460 gcaatcaaat gggagtatgt cgtgttgctc ttccttctcc tggcagacgc gcgcgtctgt    2520
```

-continued

```
gcctgcttgt ggatgatgct gctgatagcc caagctgagg ccgccttaga gaacctggtg    2580
gtcctcaatg cagcgtccgt ggccggagca catggcattc tctccttcct tgtgtttttc    2640
tgtgctgcct ggtacatcaa gggcaggctg gtccctggag cggcatatgc tatctatggc    2700
gtatggccgc tactcctgct cctgctggcg ctaccaccac gggcatacgc cttggaccgg    2760
gagatggctg catcgtgcgg aggcgcggtt ttcgtaggtc tggtactctt gaccttgtca    2820
ccacactata aagagttcct cgccaggctt atatggtggt tgcaatacta catcaccaga    2880
gccgaggcgc tactgcaagt gtggatcccc cccctcaatg ttcgggggggg ccgcgacgcc    2940 atcatcctcc tcacgtgtgt ggtccaccca gagctaattt ttgacatcac caagctcttg    3000
ctcgccatgc tcggcccgcc catggtgctc caggctgtca taaccaaggt gccgtacttt    3060
gtgcgcgctc aagggctcat cgtgcatgc atgttggtgc ggaaagtcgc tgggggccat    3120
tacgtccaaa tggctctcat gaagctggcc gggttgacaa gcacgtacgt ttatgaccat    3180
cttactccgt tgcaggactg ggcccacggc ggcctacgag acctcgcggt ggcagttgag    3240
cccgttgttt tttctgacat ggagaccaag atcatcacct gggggggcgga cactgcggcg    3300 tgtggtgaca tcatctcggg gttacctgtc tccgcccgaa gggggaggga gatactcctg    3360
ggaccggccg atagtcttaa agagcaggga tggcgactcc ttgcacccat cacggcttac    3420
tcccaacaga cgcggggcct acttggttgc atcatcacta gcctcacagg ccgggacaag    3480
aaccaggtcg aggggaggt tcaagtggtc tccaccgcaa cacaatcttt cctggcgacc    3540
tgtgtcaacg gcgtgtgttg gactgtgtat catggcgccg gctcaaagac cctagccggc    3600
ccaaaaggtc cagtcaccca aatgtacacc aatgtagacc aggacctcgt cggctggccc    3660
gcgccccccg gggcgcgttc cttgacacca tgcacctgtg gcagctcgga cctttacttg    3720
gtcacgagac atgccgatgt catcccggtg cgccggcggg gcgacagcag gggaagccta    3780
ctctccccca ggcccgtctc ctacttgaag ggctcttcgg gtggtccatt gctctgcccc    3840
tcggggcacg ctgtgggcat cttccgggct gctgtgtgca cccgggggt cgcgaaggcg    3900 gtggactttg tgcccgttga gtctatggaa actactatgc ggtctccggt cttcacggac    3960
aattcatctc ccccggccgt accggagaca ttccaggtgg cccatctaca cgctcccacc    4020
ggtagcggca agagcactaa ggtgccggct gcatatgcag ctcaagggta caaggtactc    4080
gtcctgaacc cgtccgttgc cgccacccta ggctttgggg cgtacatgtc caaggcacat    4140
ggtaccgacc ccaacatcag aactggggta aggaccatca ccacgggcgc tcccattacg    4200
tactccacct atggcaagtt cctcgccgat ggtggttgtt ctggggggcgc ctatgacatt    4260 ataatatgtg atgagtgcca ctcaactgac tcgactacca tcctgggcat tggcacagtc    4320
ctggaccaag cggagacggc tggagcacgg ctcgtcgtgc tcgccaccgc tacgcctccg    4380
ggatcggtca ccgtgccgca tcccaacatc gaggaggtgg ccctgtccaa cattggagag    4440
atccccttct atggcaaagc catccccatt gaaaccatca ggggggaag acacctcatt    4500 ttctgccatt ccaagaagaa gtgtgacgag ctcgctgcaa agctgtcggg cctcggactc    4560
aacgctgtag cgtattaccg gggccttgac gtgtccgtca taccgaccag cggagacgtc    4620
gttgtcgtag caacagacgc tctaatgacg ggctttaccg gcgactttga ctcagtgatc    4680
gactgtaaca catgtgtcac ccaaacagtc gatttcagct tggaccctac cttcaccatt    4740
gagacgacga ccgtgcccca agacgcagtg tcgcgctcgc aacggcgagg caggactggt    4800
aggggcagga gaggcatcta caggtttgtg actccgggag agcggccctc gggcatgttc    4860
gattcctcgg tcctgtgtga gtgctatgac gcgggctgtg cttggtatga gctcacgccc    4920
```

```
gccgagactt cggttaggtt gcgggcttac ctaaacacac cagggttgcc cgtctgccaa    4980
gaccacctgg agttctggga gagcgtcttc acaggcctca cccacataga cgcccacttc    5040
ttgtcccaga ccaaacaagc gggagagaac ttcccctacc tgacagcgta ccaggccaca    5100
gtgtgtgcca gggctcaggc tccacctcca tcgtgggatc aaatgtggaa gtgtctcata    5160
cggctaaagc ctacgctgca cgggccaaca cccctgctgt ataggctagg agccgtccaa    5220
aacgaggtcg tccttacaca ccccataacc aaatacatca tggcatgcat gtcggctgac    5280
ctagaggtcg tcacgagcac ctgggtgcta gtgggcggag tcctcgcagc cctggctgcg    5340
tattgcctga caacgggcag cgtggtcatt gtgggcagga ttatcttgtc cgggaggccg    5400
gctatcattc ccgacaggga agtcctttac caggagttcg atgagatgga agagtgcgcc    5460
tcacaccttc cttacatcga cagggaatg cagctcgccg aacaattcaa acagaaggcg    5520
ctcgggttgc tgcagacagc cactaagcaa gcggaggctg ctgttcccgt ggtggaatcc    5580
aagtggcaag cccttgaggc tttttgggcg aagcacatgt ggaacttcat cagcgggata    5640
cagtacttag caggcttgtc cactctgcct gggaaccctcg caatagcatc actgatggca    5700
ttcacagcct ccatcaccag cccgctcacc acccaacata ccctcctgtt taacatcttg    5760
ggggatgggt ggctgcccca actcgctccc cccagcgccg cctcagcttt cgtaggcgcc    5820
ggcatcgccg gtgcggccgt tggcagcata ggccttggga aggtgcttgt ggacatcctg    5880
gcgggctatg agcaggagt ggctggcgcg ctcgtggcct ttaaagtcat gagcggcgag    5940 atgcccctcca ccgaggacct ggtcaactta ctccctgcca tcctctctcc tggcgccctg    6000
gtcgtcgggg tcgtgtgcgc agcaatactg cgtcggcatg tgggccctgg ggaggggct    6060 gtgcagtgga tgaaccggct gatagcgttc gcttcgcggg gtaaccacgt gtcccccacg    6120
cactatgtgc ctgagagcga cgccgcagcg cgtgtcactc agatcctctc cagccttacc    6180
atcacccagc tgttgaagag gctccaccag tggattaacg aggactgctc cacgccatgc    6240
tccggttcgt ggctaaggga tgtttgggac tggatatgca cggtgttgac tgacttcaag    6300
acctggctcc agtccaagct cctgccacgt taccgggaa tcccttttta ctcatgccag    6360
cgtgggtaca agggagtatg gcggggagac ggcatcatga aaaccacctg cccatgtgga    6420
gcacagatca ctggacatgt caaaaacggt tccatgagga tcgttgggcc taaaacctgc    6480
agcaacacgt ggcacggaac attccccatc aacgcataca ccacgggccc ctgcacaccc    6540
tccccggcgc caaactattc tagggcgctg tggcgggtgg ctgctgagga gtatgtggag    6600
gttacgcggg tgggggattt ccactacgtg acgggcatga ccactgacaa cgtaaaatgc    6660
ccatgccagg ttccggctcc cgaattcttc acggaggtgg atgggtgcg gctgcacagg    6720 tacgcccccg cgtgcaaacc cctcctacgg gatgaagtca cattccaggt cgggctcaac    6780
caatacgtgg ttgggtcaca actcccatgc gagcccgaac cggatgtagt ggtggtcact    6840
tccatgctta ccgacccctc ccacattaca gcagagacgg ctaagcgtag gctgacagg    6900 gggtctcccc cctccttggc cagctcttca gctagccagt tgtctgcgcc ttccttgaag    6960
gcgacatgca ctacccgtca cgactcccca gacgctgacc tcattgaggc caacctcctg    7020
tggcggcagg agatgggcgg aaacatcacc cgcgtggagt ctgaaaacaa ggtagtaatt    7080
ctggactctt tcgacccgct tcgagcggag gaggatgaga gggaagtatc cgtcgcggcg    7140
gagattctgc ggaaatccag gagattcccc cgagcgatgc ccatatgggc acggccggat    7200
tacaaccccc cactgctaga gtcctggaag gatccggact acgtccctcc ggtggtgcac    7260
```

```
gggtgcccat taccacctac caaggcccct ccaataccac ctccacggaa aaagaggacg    7320
gttgtcctga cagagtccac cgtgtcttct gccttggcgg agcttgctac aaagaccttc    7380
ggcagctccg aatcgtcggc cgtcgacagc ggcacggcga ccgcccctcc tgaccagccc    7440
cccgacaacg acgacacagg atccgacgtt gaatcgtgct cctccatgcc ccccttgag     7500 ggggagccgg gggatcccga tctcagcgac gggtcttggt ctaccgtgag cgaggaggct    7560
agtgaggacg tcgtctgctg ttcgatgtcc tacacgtgga cgggcgctct gatcacacca    7620
tgcgccgcgg aagaaagcaa gctgcccatc aatgcgttga gcaactcttt gctgcgtcat    7680
cacaacatgg tgtacgccac aacctcccgc agcgcaagcc agcggcagaa gaaggtcact    7740
tttgacagac tgcaagtcct ggacgaccac taccgggacg tgctcaagga gatgaaggcg    7800
aaggcgtcca cagttaaggc taaacttcta tccgtagaag aagcctgcaa gctgacaccc    7860
ccacattcgg ccagatctaa atttggctac ggggcgaagg acgtccggaa cctatccagc    7920
aaggccgtta accacatccg ctccgtgtgg aaggacttgc tggaagacac tgaaacacca    7980
attgatacta ccatcatggc aaagaatgag gtcttctgcg tccaaccaga aaaaggaggc    8040
cgcaagccag ctcgccttat cgtgttccca gacttggggg tgcgcgtatg cgagaagatg    8100
gctctttatg acgtggtctc cacccttcct caggccgtga tgggcccctc gtacggattt    8160
cagtactctc ctggacagcg ggtcgagttc ctggtaaatg cctggaaatc aaagaagtgt    8220
cctatgggct tcgcatatga cacccgctgt tttgactcaa cggtcactga gagtgacatc    8280
cgtgttgagg agtcaattta ccaatgttgt gacttggccc ccgaagccag acaggccata    8340
aagtcgctca cagagcggct ttacatcggg ggtcccctga ctaattcaaa agggcagaac    8400
tgcggttatc gccgatgccg cgcaagcggc gtgctgacga ctagctgcgg taataccctt    8460
acatgttact tgaaggcctc tgcggcctgt cgagctgcaa agctccagga ctgcacgatg    8520
ctcgtgtgcg agacgacct cgtcgttatc tgtgaaagcg cgggaaccca agaggacgcg    8580
gcgagcctac gagtcttcac ggaggccatg actaggtact ctgccccccc cggggacccg    8640
ccccaaccag aatacgacct ggagctgata acatcatgct cctcgaatgt gtcggtcgcg    8700
cacgatgcat ccggcaagag agtatactac ctcacccgtg accccaccac cccccttgcg    8760
cgggctgcgt gggagacagc tagacacact ccagttaact cctggctagg caacatcatc    8820
atgtatgcgc ccactttgtg ggcgaggatg attctgatga cacacttctt ctccatcctt    8880
ctagctcagg aacaacttga aaaagcccta gattgtcaga tctacggggc ctgttactcc    8940
atagagccac ttgacctacc tcaaatcatt cagcgactcc atggtcttag cgcattttca    9000
ctccacagtt actccccagg tgagatcaat agggtggctt catgcctcag gaaacttggg    9060
gtaccgccct tgcgagcctg gagacatcgg gccagaagtg tccgcgctaa gctactgtcc    9120 cagggggaa gggctgccac ttgtggccgc tacctcttca ctgggcagt aaagaccaaa       9180 cttaaactca ctccaattcc ggctgcgtcc cagttggact tgtccaactg gttcgttgct    9240
ggttacagcg ggggagacat atatcacagc ctgtctcgtg cccgaccccg ctggttcatg    9300
tggtgcctac tcctactttc tgtaggggta ggcatctacc tgctccccaa ccgatgaacg    9360
gggagctaac cactccagg                                                 9379
```

<210> SEQ ID NO 157
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 157
gtgatgttac cgcccatctc                                               20

<210> SEQ ID NO 158
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 158
gygargcraa cgctatcag                                                19

<210> SEQ ID NO 159
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 159
ratgacrtcg gcrtgcct                                                 18

<210> SEQ ID NO 160
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 160
tayttygtgc gcgtyca                                                  17

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 161
tcagtagtca tgcccgtcac                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 162
tcagyagtca trcccgtyac                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 163
tcccrratgg agaccaarct                                               20

<210> SEQ ID NO 164

<210> SEQ ID NO 164
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 164
tcctcaactt ccggcattac                                         20

<210> SEQ ID NO 165
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 165
tcctcractt ccggyatyac                                         20

<210> SEQ ID NO 166
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 166
tcctggctaa gggacatctg                                         20

<210> SEQ ID NO 167
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 167
tcgayttcag yttggaycc                                          19

<210> SEQ ID NO 168
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 168
tcrgcygaca tgcatgycat gat                                     23

<210> SEQ ID NO 169
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 169
tggatgatgy tactcatatc cca                                     23

<210> SEQ ID NO 170
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 170
tggcacagtg accgatcc                                                  18

<210> SEQ ID NO 171
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 171
tggcacrgtr acygatcc                                                  18

<210> SEQ ID NO 172
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 172
tgtrttyagg targcccg                                                  18

<210> SEQ ID NO 173
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 173
ttccacatrt gcttcgccca                                                20

<210> SEQ ID NO 174
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 174
ttctcrtatg ayaccgctg ytttga                                          26

<210> SEQ ID NO 175
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 175
ttgcrccyat cacrgcyta                                                 19

<210> SEQ ID NO 176
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 176
tttggatctg gctgaatgtg                                                20

<210> SEQ ID NO 177
<211> LENGTH: 19
<212> TYPE: DNA

```
<213> ORGANISM: Artificial Sequence
<220> FEATURE:
<223> OTHER INFORMATION: Synthetic Oligomer

<400> SEQUENCE: 177
tyctygtgga catycttgc                                                  19

<210> SEQ ID NO 178
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 178
yggcagctcg gayctyta                                                   18

<210> SEQ ID NO 179
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 179
ggttgacggc cttgctggat a                                               21

<210> SEQ ID NO 180
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 180
ggttgacggc cctgctggat a                                               21

<210> SEQ ID NO 181
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 181
ggttaacggc cytgctggat a                                               21

<210> SEQ ID NO 182
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 182
ggttaacggc cttgctggat a                                               21

<210> SEQ ID NO 183
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 183
ggttaacggc cctgctggat a                                               21
```

```
<210> SEQ ID NO 184
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 184
tacctvgtca tagcctccgt gaa                                          23
```